United States Patent
Timko et al.

(10) Patent No.: US 10,280,203 B2
(45) Date of Patent: May 7, 2019

(54) COMPOSITIONS AND RELATED METHODS FOR MODULATING ALKALOID PRODUCTION BY CONTROLLING PMT PROMOTER ACTIVATION MEDIATED BY TRANSCRIPTIONAL FACTORS ERF AND MYC

(71) Applicant: University of Virginia Patent Foundation, Charlottesville, VA (US)

(72) Inventors: Michael Paul Timko, Charlottesville, VA (US); Paul J Rushton, Brookings, SD (US); Sheng-Cheng Han, Charlottesville, VA (US); Hongbo Zhang, Chongging (CN); Marta Tatiana Bokowiec, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/644,199

(22) Filed: Jul. 7, 2017

(65) Prior Publication Data
US 2017/0306342 A1    Oct. 26, 2017

Related U.S. Application Data

(60) Division of application No. 14/311,684, filed on Jun. 23, 2014, now Pat. No. 9,701,978, which is a continuation of application No. 12/676,871, filed as application No. PCT/US2008/010447 on Sep. 5, 2008, now Pat. No. 8,759,101.

(60) Provisional application No. 60/935,948, filed on Sep. 7, 2007, provisional application No. 60/935,947, filed on Sep. 7, 2007.

(51) Int. Cl.
  *C12N 15/82*  (2006.01)
  *C07K 14/415* (2006.01)

(52) U.S. Cl.
  CPC ........ *C07K 14/415* (2013.01); *C12N 15/8239* (2013.01); *C12N 15/8243* (2013.01)

(58) Field of Classification Search
  None
  See application file for complete search history.

(56) References Cited

U.S. PATENT DOCUMENTS 8,624,083 B2   1/2014  Page et al.
8,759,101 B2   6/2014  Timko et al.
9,157,089 B2 * 10/2015  Page .................... C07K 14/415

FOREIGN PATENT DOCUMENTS

WO    WO 2000/067558    11/2000

OTHER PUBLICATIONS

Zhang et al, 2012, Molecular Plant, 5:73-84.*
De Boer et al, 2011, Plant. J., 66:1053-1065.*
De Boer et al., APETALA2/Ethylene Response Factor and basic helix-loop-helix tobacco transcription factors cooperatively mediate jasmonate-elicited nicotine biosynthesis, 66 The Plant Journal 1053-1065 (2011).
Sato et al., Metabolic engineering of plant alkaloid biosynthesis, 98(1) PNAS 367-372 (Jan. 2, 2001).
Todd et al., A functional genomics screen identifies diverse transcription factors that regulate alkaloid biosynthesis in Nicotiana benthamiana, 62 The Plant J. 589-600 (2010).
B. Xu et al., Methyl jasmonate induced expression of the tobacco putrescine N-methyltransferase genes requires both G-box and GCC-motif elements, 55 Plant Molecular Biology 743-761 (Jul. 2004).
H. Zhang et al., Tobacco Transcription Factors NtMYC2a and NtMYC2b Form Nulcear Complexes with the NtJAZ1 Repressor and Regulate Multiple Jasmonate-Inducible Steps in Nicotine Biosynthesis, 5(1) Molecular Plant 73-84 (Jan. 2012).
Altschul et al., Local alignment statistics, 266 Methods in Enzymology 460-80 (1996) (abstract only).
Altschul et al., Basic local alignment search tool, 215 J. Mol. Biol. 403-10 (1990) (abstract only).
Corpet, Multiple sequence alignment with hierarchical clustering, 16 Nucleic Acids Res. 10881-90 (1988).
Higgins et al., CLUSTAL: a package for performing multiple sequence alignment on a microcomputer, 73 Gene 237-244 (1988) (abstract only).
Higgins et al., Fast and sensitive multiple sequence alignments on a microcomputer, 5(2) Comput Appl. Biosci. 151-153 (1989).
Huang et al., Parallelization of a local similarity algorithm, 8 CABIOS 155-65 (1992).
Karlin et al., Applications and statistics for multiple high-scoring segments in molecular sequences, 90 Proc. Natl. Acad. Sci. 5873-87 (1993).
Pearson et al., Using the Fasta Program to Search Protein and DNA Sequence Databases, 24 Meth. Mol. Biol. 307-331 (1994) (abstract only).
http://www.biology.wustl.edu/gcg/blast.html (Printed on Oct. 15, 2018).

* cited by examiner

*Primary Examiner* — Jason Deveau Rosen
(74) *Attorney, Agent, or Firm* — Buchanan Ingersoll & Rooney LLP

(57) ABSTRACT

Compositions and methods for modifying the production levels of alkaloids in plants are provided. Alkaloid production can be genetically controlled by modulating the transcriptional activation of PMT genes mediated by members of the ERF family and/or Myc family of transcription factors. Novel nucleotide sequences encoding the Myc family of transciption factors are also provided.

6 Claims, 16 Drawing Sheets
Specification includes a Sequence Listing.

NtERF5 and NtERF2 are MeJA responsive, but with different kinetics

NtERF3 is ethylene responsive

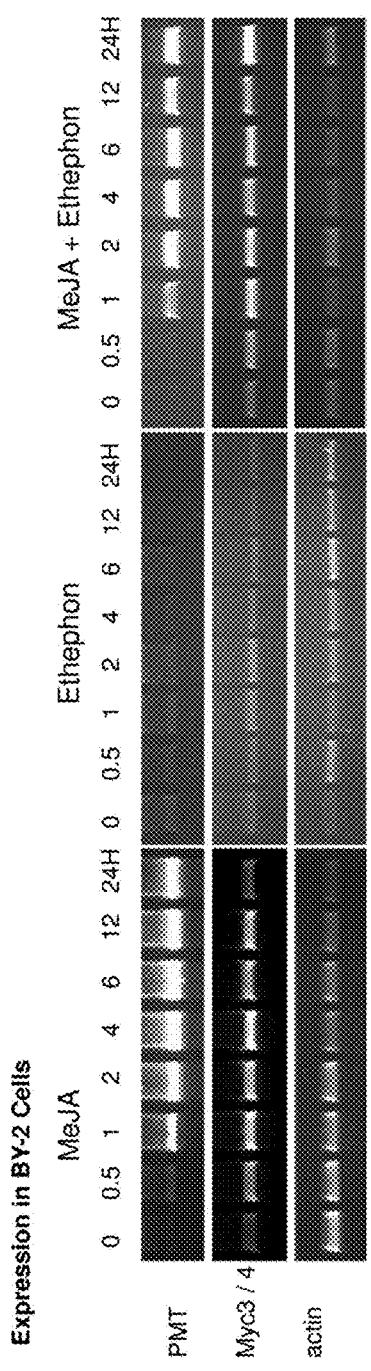
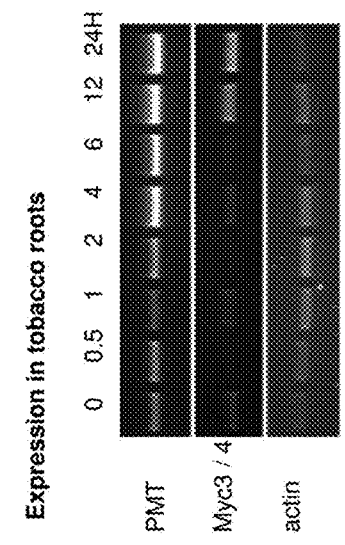
FIG. 8A
FIG. 8B
FIG. 8C
FIG. 8D

Myc 3 protein
GAG (G-box intact)
GAG (mG-box)

G-Box: CTGCACGTTGTAAT (SEQ ID NO:9)

Mutant G-box: CTGCTTAATGTAAT (SEQ ID NO:10)

Probe + Myc3 (monomer)

Free probe

FIG. 9

NtMYC3 cDNA Sequence:

ATGACTGATTACAGCTTACCCACCATGAATTTGTGGAATACTAGTGGTACTACCGATGATGACAACGTTTCTATGAT
GGAATCTTTTATGTCTTCTGATCTCACTTGATCTCATTTGGGCTACTTCTAATTCTACTACTGCTGTGTTACCTCTAA
TTCTAATCTTATTCCAGTTAATACCCTAACTGTCTTCTTCCGTGTCTTCTCTGTGCTTCTACTGTCACAGCTGTGG
CTGTCGATGCTTCAAATCCATGTCTTTTTCAACAAGAAACTCTTCAGCAGCGTCTCAAACCCTCATTGAT
GGTGCTCGTGAGACGTGGACCTATGCCATCTTTTGACCAGTCGTCATTCGTGTTGATTTATGAGTCGTTTGTG
TTGGGCTGGGGAGATGGTTACTACAAGGTGAAGAAGTTCTCCGGGAGCTGAATTGGTTGATCTCCGGCAGCAA
GCTTATATTGCTGAGCAAACCGGAAAAAAGGTTCTCCGGGAGCTGAATTGGTTCTTCCTTATTTGGGCGCGCAA
ACCGGCACTGATGATGCCGTGATGGGCTTCCGGCGAACACGGGCTCGGCAGAAGAAGTTACCGACCCTTATACAACGACCCAAT
CGTTGTTAACGGAAGTGGGCTTCCCACTGCGGTTGGCTCGGCAGGCTCAGCGTTGGGCTTCAGAGTTGTGATCTCATGAAC
AGAAATTGGCAGCTTCAATATGTTAACTTCAATATTGGGCTCTGTGCAGTTGATAATCCAGAGTTGTGATCCGAGAGTTGT
ATCCTTCAGCAAACGGCTCTTTGGCTCACTGATCCATCGTCTGCAGTAAGCAAGTTGTTTGATAATGAGAGGCAGT
AAGGTTAGAGTATTGTTAACTTCAATATTGTTGCTCACTGATCCATCGTCTGCAGTAAGCAAGTTGTTTGATAAT
CCGTCCGCTCTTTGGCTCACTGATCCATCGTCTGCAGTAAGCAAGTTGTTTGATAATGAGATAATGGTCACAGTTCTGATAT
ATTCAGTTCCATCAGCAGCATTCTAAGCATGAAACACAAGGATTTCACAAGGGAGTGAATTTTCAGAATTTGGT
CAGCAACAGCAGCATTCTAAGCATGAAACACAAGGATTTCACAAGGGAGTGAATTTTCAGAATCTTGAA
TTGATGGAAGTAGTAGTACTAAGAAAGGGAACTGCAAATGTCACCTGCTTCTGGTCGATGAAGCAATGAAGCAAT
GGAGAATAAGAACAAGAAAGGTCACCTGCTTCTGGTCGATGAAGCTGAAGAAGTCAAGTGGAGGTGTAGAACCCG
GGGTACAATCTTGCCTGCAGCTTCTGTGAAAGAAGCTGAAGAAGTCAAGTGGAGGTGTAGAACCCGAAAGAGGCCAAAGGA
GGATCTTGAGGCCTCAGTGGTGAAGAAGCTGAAGAAGTCAAGTGGAGGTGTAGAACCCGAAAGAGGCCAAAGGAGA
GCGGAAGGAAGCCAGCAAAGGTTCTACGCATTAAGAGACTGTTGTTCCGAATGTGTCCAAATACGAGACAAGGCATCAC
GAGAAATTAACCAAAGGTTCTACGCATTAAGAGACTGTTGTTCCGAATGTGTCCAAATACGAGACAAGGCATCAC
TGCTTGGAGATGCAATTTCATTAATGAGCTGAAGTTGAAGTTGTAGTACGAAGAATTAGTAGTACGAAGATTAGTAGAA
ATTGAAGAGCCAAATAGAAGATTTAAGAAGATTGAAGTTGAAGTTAGTAGTACGAAGATTAGTAGCTCCACCA
TCAAATCATGATCATCACAAGATGTCTAGCCATACAATGTAATAAAAAGAATCATCCAGCTGCAAGTTAATGGTAAGATAA
TTGGATGGGATGCGATGATTAGATCGATGTGCCACATGCCAGTGTTTCAGTGGTGATCGAACAAGCACT
CAAGGGAGTTGACACTTTACACGGAAGAGCAACTTAGGATAGCATTGACATTGACATTGACATCCAGAGTTGCTGAAACA
CGCTAA

FIG. 11

NtMYC3 Protein:

MTDYSLPTMNLWNTSGTTDDNVSMMESFMSSDLTSFWATSNSTTAAVTSNSNLIPVNTLTVLLP
SSCASTVTAVAVDASKSMSFFNQETLQQRLQTLIDGARETWTYAIFWQSSVVDLSSPFVLGWGD
GYYKGEEDKANRKLAVSSPAYIAEQEHRKKVLRELNSLISGTQTGTDDAVDEEVTDTEWFFLISM
TQSFVNGSGLPGQALYNSSPIWVAGAEKLAASHCERARQAQGFGLQTMVCIPSANGVVELGST
ELIIQSCDLMNKVRVLFNFNNDLGSGSWAVQPESDPSALWLTDPSSAAVEVQDLNTVKANSVPS
SNSSKQVVFDNENINGHSSDNQQOHSKHETQGFFTRELNFSEFGFDGSSNNRNGNSSLSCKP
ESGEILNFGDSTKKSANGNLFSGQSHFGAGEENKNKKRSPASRGSNEEGMLSFVSGTILPAASG
AMKSSGGVGEDSDHSDLEASVVKEAESSRVVEPEKRPKKRGRKPANGREEPLNHVEAERQRR
EKLNQRFYALRAVVPNVSKMDKASLLGDAISYINELKLKLQNTETDREELKSQIEDLKKELVSKDS
RRPGPPPSNHDHKMSSHTGSKIVDVDIDVKIIGWDAMIRIQCNKKNHPAARLMVALKELDLDVHH
ASVSVVNDLMIQQATVKMGSRLYTEEQLRIALTSRVAETR

FIG. 12

NtMYC4 cDNA Sequence:

```
ATGACTGATTACAGCTTACCCACCATGAATTTGTGGAATACTAGTGGTACTACCGATGACAAGTTACTATGA
TGGAAGCTTTATGTCTTCTGATCTCACTTCATTTGGGCTACTTCTAATTCTACTGCTGTTGCTGTTACC
TCTAATTCTAATCATATTCCAGTTAATACCCAACGGTTCTTCTTCCGTCTCTTGTGCCTCTACTGTCACAGC
TGTGGCTGTCGATGCTCAAATCCATGTCTTTTCAACCAAGAAACCCTCAACAGGTCTTCAAACGCTCA
TTGATGGTGCTCGTGAGACGTGGACCTATGCCATCTTTGGCAGTCATCCGCGTTGATTAACGAGTCCGT
TGTGTTGGGCTGGGAGATGCTACTACAAGGTGAAGAAGTAAAGCCAATAAGGAATTAGCTGTTTCTTC
TCCTGCTTATATAGCTGAGCAAGAACACCGGAAAAAGGTTCTCCGGAGCTGAATTGGTTGATTTCCGCAC
GCAAACCGGCACTGATGCCGTCGATGAAGTGCCTCAGGCTTACCGACACTGAATGGTTCTCCTATTCCATGACC
CAGTCGTTTGTTAACGGCAGCTTCCACTGCGAACGGTGGGCTCGGCTCCACGGAGTTGAATTCAGCCCTATTGGGCTGCCGGA
GCAGAGAAATTGGCAGCTTCAGCAACGGGTCGTGGTTAACTTCAATAATGATTGGGCTCGGTTCTGATCCAT
TTTGTATTCCTCAGCAAGGTATATTGTTAACTTCAATAATGATTTGGCTGTGCTGTGCAACCGAGAG
GAACAAGGTTAGAGTATTCCGCTCTTGGCTCACTGATCCATCGTCAGTTGATCAAGATTAATAATACAGTTGAG
CGATCCGTCGTCTCTTGGCTCACTGATCCATCAGTAGTAAGCAAGTGTATTTGATAATGAGAATAATGGTCACAGTTGTGA
GCAAATTCAGTTCCATCAAGTAATAGTAAGCAAGATAAGAACAACAAGGATTTTTACAAGGAGTTGAACTTTTCAGAATTC
TAATCAGCAACAGCACCATTCTCGGCAACAAAGTCACAAGGAATCATCACTTCTTGCAAGCCAGAGTCAGTCTCATTTGGTGCAG
GGGTTTGATGGAAGTGATAGCACTAAGAAAAGTGCAAATGGAAATAAGTCACCTGCTTCCAGAGGAATGAAGAAGGAATGCTTCATTG
TTCAGGAGAGAATAAGAAGAAGGAGACCAGAAGCCAGAAATGGACCTCTCGGTAAGGCTCAGTGAAGTCAAGTAGTAGAGTTCGGTGAAGACTCCTG
ATCATTCGGATCTTGAGGCTGCAGTCTCAGTGTGAAAGACTTTAAGAATCTCTAAGAGCTGAAGCTTCGGTGAGAACCCGAAAGAGGC
CAAGGAAGCAGGAAGGAAAAAACCAAGTTAACCAAGATCAACACCAGAAATGGACCAGCTTGAATCACGTCAAGCAGAGGCAA
AGGAGAGAGAATTAAACCAAGGTTCTACCGTTAGAGCTGAAGACGTAGTGTCCAAGATGTGTGCCAAGATGGACAAG
GCATCACCTGTTGAAGATGCAAATCAAGATGGATCGATCTAGATGCATTGATGTCACCAGTCTCAAACAAACAGATA
GAGAAGACTTGAAGCCAAATCAAGATCACAAGATGGATCGATCTAGATGTGCACCAGTCTTCAATTTGGGATATAGATGT
CTCCACCACAGATAAGCCCATATGGACAGTCTCTAGCTACCATACGTGAACTGTAATAAAAGAACCCATCGAATTGATCCAAC
TAAGATAATTGGATGGAGTTAGATCTAGATGTGCGATCTAGATGTGCCAGTGTTTCAGTGGTGACAGTTGATGATCCAAC
GTAGCCCTCAAGGAACTGTGAAATGGGGTAGAGCTCAAGGGTTAGGATATAGCCATTGACATTGACATTCCAGAGTTG
CTGAAAACAGGCTAA
```

FIG. 13

NtMYC4 Protein:

MTDYSLPTMNLWNTSGTTDDNVTMMEAFMSSDLTSFWATSNSTAVAAVTSNSNHIPVNTPTVLL
PSSCASTVTAVAVDASKSMSFFNQETLQQRLQTLIDGARETWTYAIFWQSSAVDLTSPFVLGWG
DGYYKGEEDKANRKLAVSSPAYIAEQEHRKKVLRELNSLISGTQTGTDDAVDEEVTDTEWFFLIS
MTQSFVNGSGLPGQALYNSSPIWVAGAEKLAASHCERARQAQGFGLQTMVCIPSANGVVELGS
TELIIQSSDLMNKVRVLFNFNNDLGSGSWAVQPESDPSALWLTDPSSAAVQVKDLNTVEANSVP
SSNSSKQVVFDNENINGHSCDNQQHHSRQQTQGFFTRELNFSEFGFDGSSNNRNGNSSLSCK
PESGEILNFGDSTKKSANGNLFSGQSHFGAGEENKKKRSPASRGSNEEGMLSFVSGTILPAAS
GAMKSSGCVGEDSSDHSDLEASVVKEAESSRVVEPEKRPKKRGRKPANGREEPLNHVEAERQ
RREKLNQRFYALRAVVPNVSKMDKASLLGDAISYINELKLKLQTTETDREDLKSQIEDLKKELDSK
DSRRPGPPPPNQDHKMSSHTGSKIVDVDIDVKIIGWDAMIRIQCNKKNHPAARLMVALKELDLDV
HHASVSVVNDLMIQQATVKMGSRLYTEEQLRIALTSRVAETR

FIG. 14

NtERF2 cDNA Sequence:

ATGTATCAACCAATTTCGACCGAGCTACCTCCGACGAGTTTCAGTAGT
CTCATGCCATGTTTGACGGATACATGGGGTGACTTGCCGTTAAAAGTT
GATGATTCCGAAGATATGGTAATTTATGGGCTCTTAAGTGACGCTTTAA
CTGCCGGATGGACGCCGTTTAATTTAACGTCCACCGAAATAAAAGCCG
AGCCGAGGAGGAGATTGAGCCAGCTACGATTCCTGTTCCTTCAGTG
GCTCCACCTGCGGAGACTACGACGGCTCAAGCCGTTGTTCCCAAGGG
GAGGCATTATAGGGCGTTAGGCAAAGGCCGTGGGGAAATTTGCGG
CGGAAATAAGGGACCCAGCTAAAAACGGCGCACGGGTTTGGCTAGGG
ACTTATGAGACGGCTGAAGAAGCCGCGCTCGCTTATGATAAAGCAGCT
TACAGGATGCGCGGGTCCAAGGCTCTATTGAATTTTCCGCATAGGATC
GGCTTAAATGAGCCTGAACCTAGACTAACCGCTAAGAGACGATCA
CCTGAACCGCTAGCTCGTCGTCAATATCATCGGCTTTGAAAATGGCTCG
CCGAAACGGAGGAGAAAAGCTGTAGCGGCTAAGAAGGCTGAATTAGA
AGTGCAAAGCCGATCAAATGCTATGCAAGTTGGGTGCCAGATGGAACA
ATTTCCAGTTGGCGAGCAGCTATTAGTCAGTTAA

FIG. 15

NtERF5 cDNA Sequence:

ATGTCAAGTAACTCAAGCCCCACTAGAAATAGACACTTCATTTCACATT
CCAACTTCTTCTTCTCCAAGATCAATCACCAATTTACAATGGATGAT
GATCTTTCTTCAATGATCCATGGTTTGATGATCAATCACCAATTAT
ACCATGTAACTCAGAGAAAGATGAAAATCATCAAGTATTTGAAGAATCC
TCAGACAATACAATCATGTCAAAGGAAGTAGCCATGGTCAAGAATTAG
AAGAGGTAACATCCCAAGAAAAAGAAGAAGAAGAAGAAAAAC
ACTATATAGGAGTTAGAAAAAGGCCATGGGGTAAATATGCAGCAGAAA
TAAGAGATTCAACAAGAAATGGAATTAGGGTTTGGTTAGGACATTTGA
TACAGCTGAAGAAGCTGCTTTAGCTTATGATCAAGCTGCATTATCGATG
AGAGGTCCTTGGTCTCTTCTTAATTTTCCATTGGAGAAAGTCAAGAAAT
CACTTGAAAAATTGAGTACTCATAAAACAAGGAGAGTGAAGCATAAAAGAAGT
TGTTCTAAAGAAAAAGAATAAAGAAACTCATAATGTTATTGTTTTGAGG
AGTAGAAGAAAAGAATAAAGAAACTCATAATGTTATTGTTTTGAGG
ACTTGGGTGCTGAGTTATTAGAAGAGCTTTTAATGACTTCATCACAACA
TTCGTGTGTCGAAGGGACTGA

COMPOSITIONS AND RELATED METHODS FOR MODULATING ALKALOID PRODUCTION BY CONTROLLING PMT PROMOTER ACTIVATION MEDIATED BY TRANSCRIPTIONAL FACTORS ERF AND MYC

CROSS-REFERENCE TO RELATED APPLICATIONS

This application is a Divisional Application of U.S. patent application Ser. No. 14/311,684, filed on Jun. 23, 2014, now U.S. Patent No. 9,701,978, which is a Continuation Application of U.S. Patent Application Ser. No. 12/676,871, filed on Nov. 10, 2010, now U.S. Patent No. 8,795,101, which is a U.S. National Stage pursuant to 35 U.S.C. § 371 of International Patent Application PCT/US2008/010447, filed on Sep. 5, 2008, and published as WO 2009/035547 on Mar. 19, 2009, which claims priority to U.S. Provisional Patent Application No. 60/935,948, filed on Sep. 7, 2007, and U.S. Provisional Patent Application No. 60/935,947, filed on Sep. 7, 2007, all of which are incorporated herein by reference in their entireties for all purposes.

BACKGROUND

Nicotine production from polyamine putrescine, a precursor of nicotine, can be produced by two pathways in plants. Putrescine can be synthesized directly from ornithine in a reaction catalyzed by the enzyme ornithine decarboxylase, or can be produced indirectly from arginine in a sequence of reactions initiated by arginine decarboxylase. The first committed step in nicotine biosynthesis is the conversion of putrescine to N-methyl putrescine by putrescine N-methyltransferase ("PMT"). N-methylputrescine is subsequently oxidized by a diamine oxidase, and is cyclized to produce a 1-methyl-$\Delta^1$-pyrrolium cation, which is subsequently condensed with nicotinic acid to produce nicotine.

There is a need for compositions and improved methods for genetically regulating the production levels of nicotine and other alkaloids in plants, including transgenic plants, transgenic tobacco plants, recombinant stable cell lines, recombinant stable tobacco cell lines, and derivatives thereof.

SUMMARY

In various embodiments, compositions and methods for modifying the production levels of nicotine and other alkaloids in plants are provided. Nicotine and other alkaloid production can be genetically modified by modulating the transcriptional activation of PMT genes mediated by members of the ERF family and/or Myc family of transcriptional factors.

BRIEF DESCRIPTION OF DRAWINGS

FIGS. 8A-8C show that Myc3/Myc4 over-expression in BY-2 cells is inducible by MeJA.

FIG. 8D shows that Myc3/Myc4 over-expression in the roots of transgenic tobacco is inducible by MeJA.

FIG. 9 shows that Myc3 binds the G-box of the GAG motif by in vitro mobility shift assay.

FIG. 11 shows the polynucleotide sequence for NtMyc3 cDNA (SEQ ID NO:1).

FIG. 12 shows the polypeptide sequence for NtMyc3 protein (SEQ ID NO:2).

FIG. 13 shows the polynucleotide sequence for NtMyc4 cDNA (SEQ ID NO:3).

FIG. 14 shows the polypeptide sequence for NtMyc4 protein (SEQ ID NO:4).

FIG. 15 shows the polynucleotide sequence for NtERF2 cDNA (SEQ ID NO:5).

FIG. 16 shows the polynucleotide sequence for NtERF5 cDNA (SEQ ID NO:6).

DETAILED DESCRIPTION

Regulation of nicotine biosynthesis is desirable in a variety of plants, especially in tobacco plants. Nicotine biosynthesis can be regulated by controlling the expression levels and/or the activities of enzymes involved in the nicotine biosynthetic pathway. In particular, an effective way to genetically regulate nicotine production is by controlling the transcriptional activation of promoters that control the expression of genes encoding putrescine N-methyltransferases ("PMT"). PMT is one of several critical enzymes involved in the nicotine biosynthetic pathway in plants, including tobacco plants. Various compositions and methods for modifying PMT expression levels in plants are provided, as further described below.

The production levels of nicotine, other alkaloids, and secondary metabolites can be genetically regulated by controlling the expression level of PMT, which correlates directly with their production levels. This can be accomplished by controlling PMT promoter activation that correlates with the expression levels of the PMT structural gene. PMT RNA transcripts produced by transcriptional processes are subsequently translated into PMT polypeptides that exhibit PMT enzymatic activity. The activation of the PMT promoter by sequence-specific transcriptional factors ("transcriptional activators") can increase the levels of PMT RNA transcripts and PMT polypeptides produced. In contrast, the repression of the PMT promoter by sequence-specific transcriptional factors ("transcriptional repressors") can decrease the levels of PMT RNA transcripts and PMT polypeptides produced.

Figure 1:
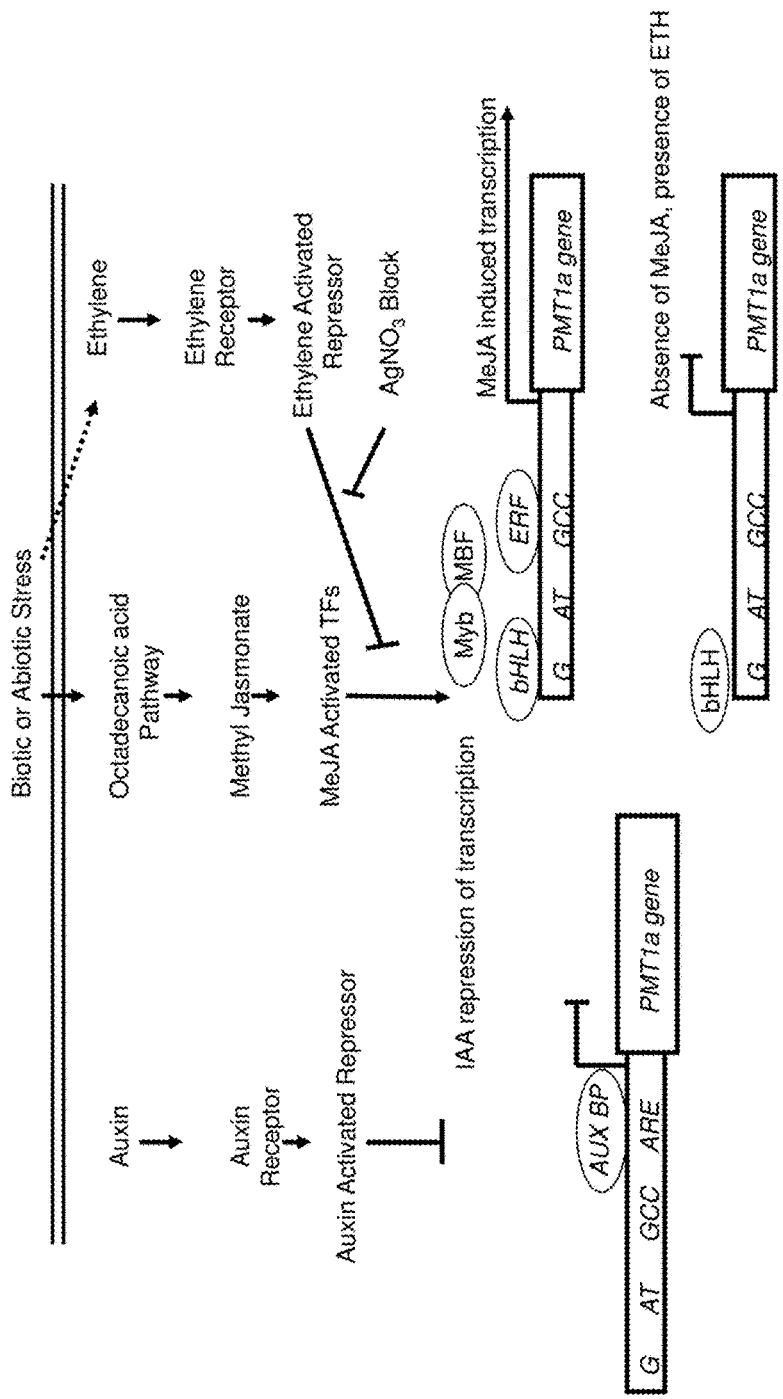
FIG. 1 illustrates multiple signal transduction pathways, induced by various stimuli that regulate PMT promoter activation/repression in plants.
Figures 2A, 2B, 2C:
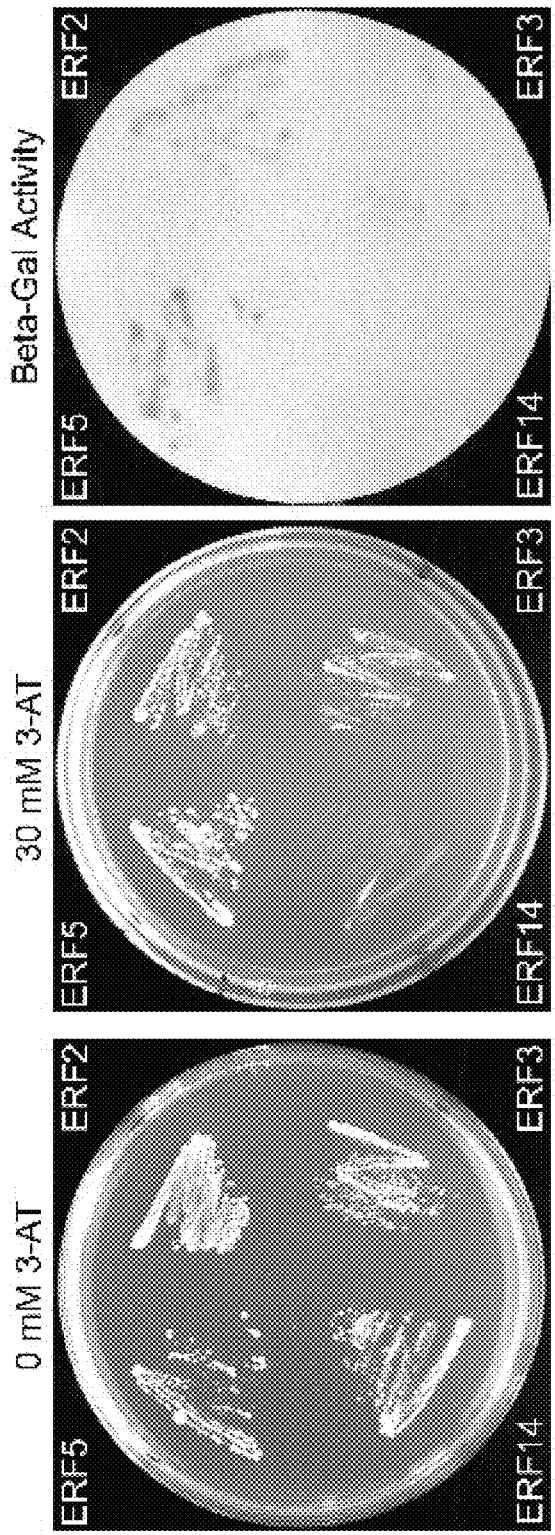
FIGS. 2A-2C show the identification of transcription factors of the ERF family that can bind specifically to the GAG motif.
Figures 3A, 3B, 3C:
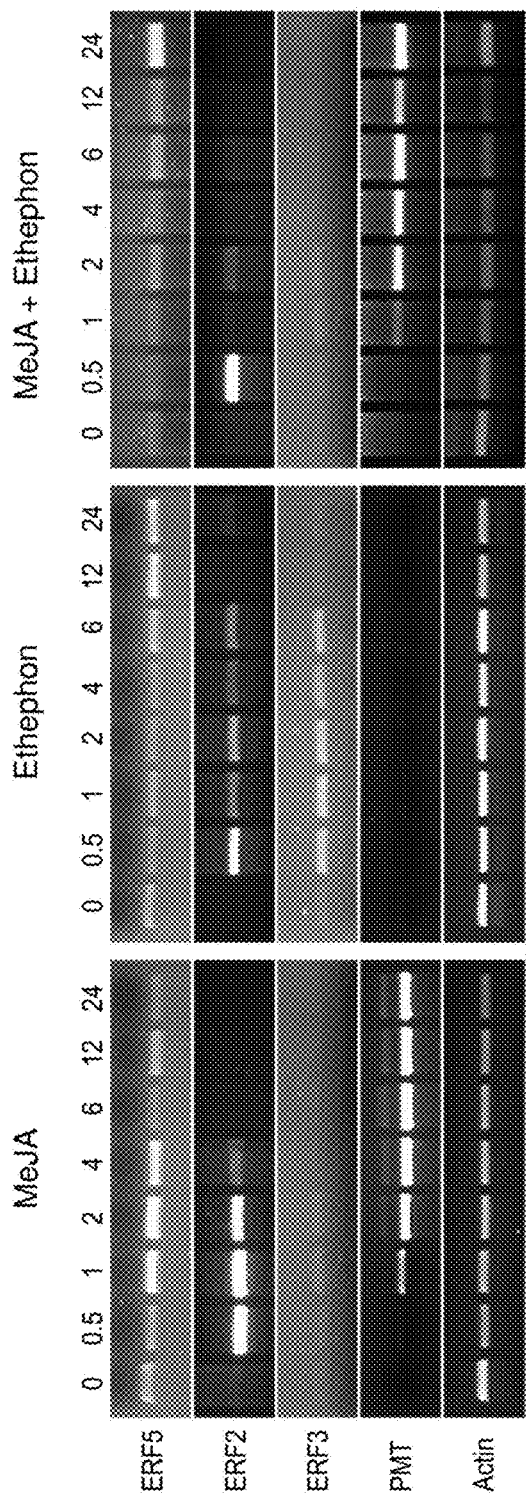
FIGS. 3A-3C show relative expression levels of transcripts for NtERF2, NtERF3, and NtERF5, measured by RT-PCR in BY-2 cell extracts. The expression levels of NtERF2 and NtERF5 were responsive to MeJA-inducible pathway. The expression level of NtERF3 was responsive to ethylene (or ethephon) inducible pathway.
Figure 4:
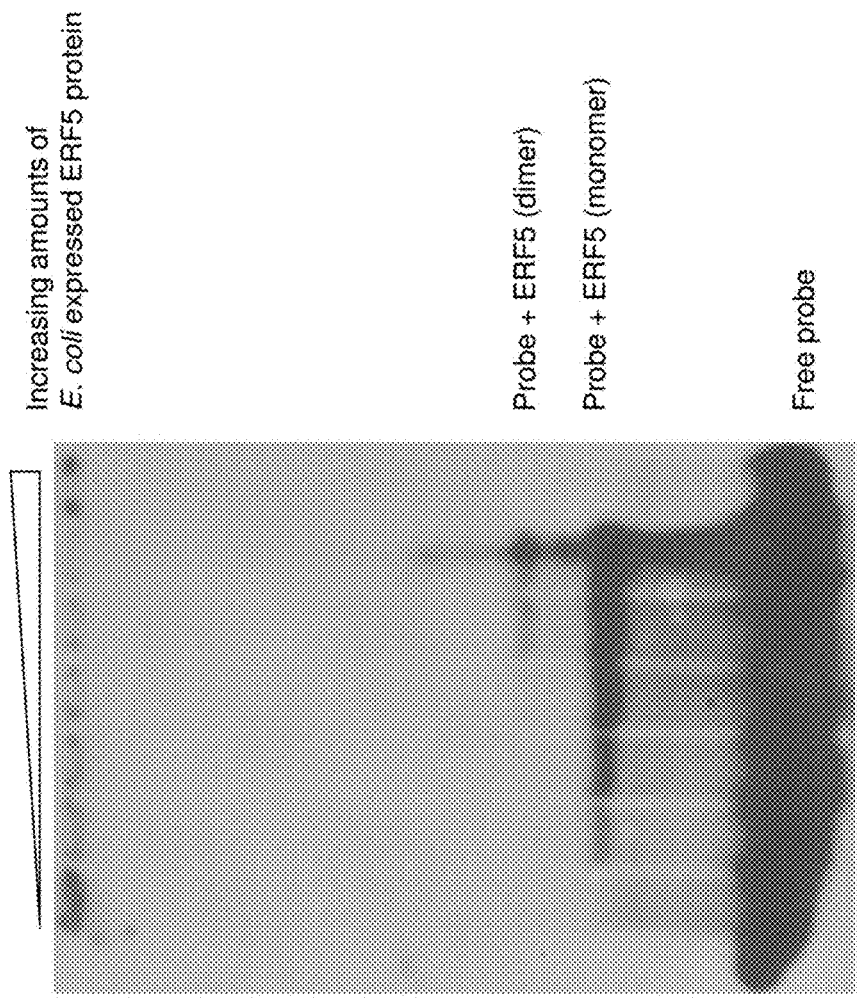
FIG. 4 shows that NtERF5 can bind to the GAG motif by in vitro gel mobility shift assay.
Figures 5A, 5B, 5C:
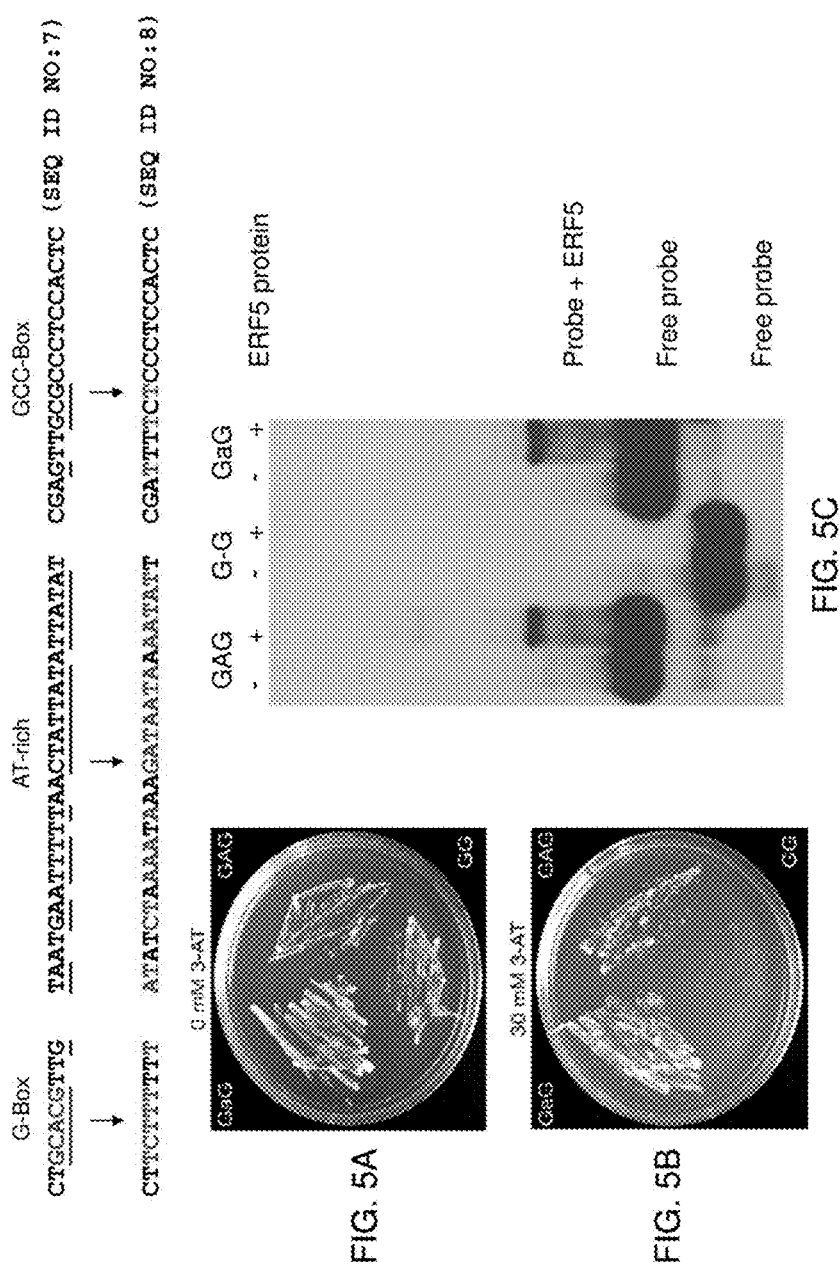
FIGS. 5A-5C show that NtERF5 can activate the NtPMT1a promoter by binding to the AT-rich region of the GAG motif.
Figure 6A:
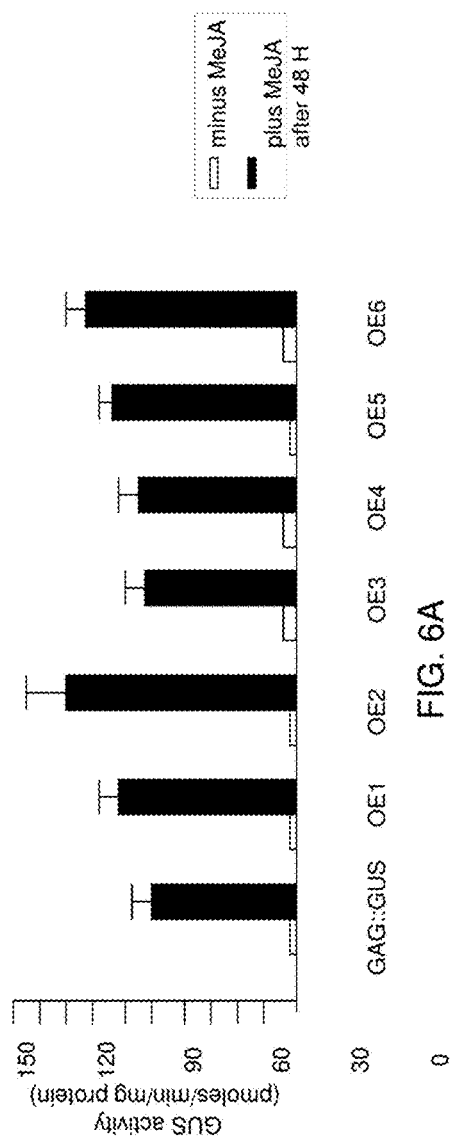
FIG. 6A shows that NtERF5 over-expression results in GUS reporter expression in a MeJA-dependent manner by binding to 4xGAG motifs positioned upstream of a promoter that drives GUS reporter expression. Overexpressed cell lines ("OE") that have been stably integrated with 4XGAG::GUS reporter were transiently transfected with expression vectors over-expressing NtERF5.
Figure 6B:
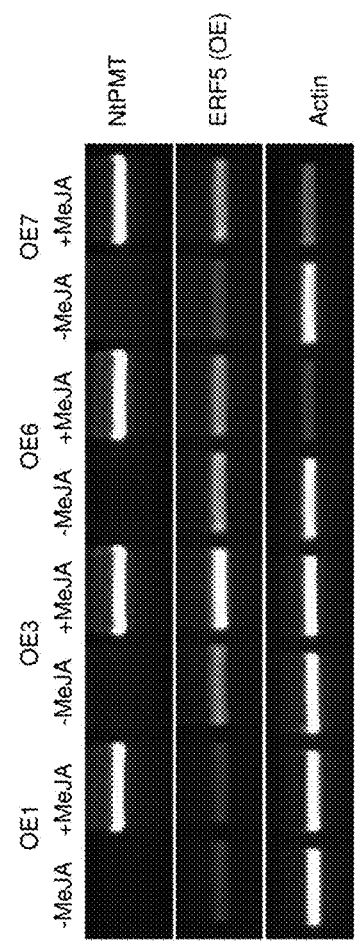
FIG. 6B shows that NtERF5 over-expression is not sufficient to activate NtPMT expression in the absence of MeJA. NtPMT transcripts were detected in extracts of cell lines that were induced by MeJA.
Figure 7:
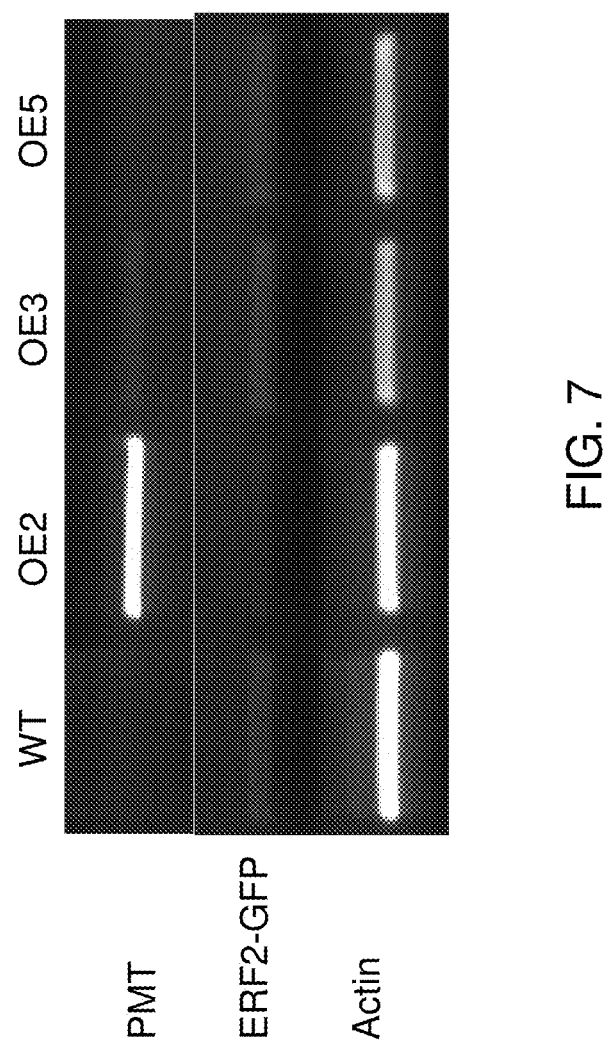
FIG. 7 shows that NtERF2 over-expression activates NtPMT expression in a MeJA-independent manner.
Figure 10:
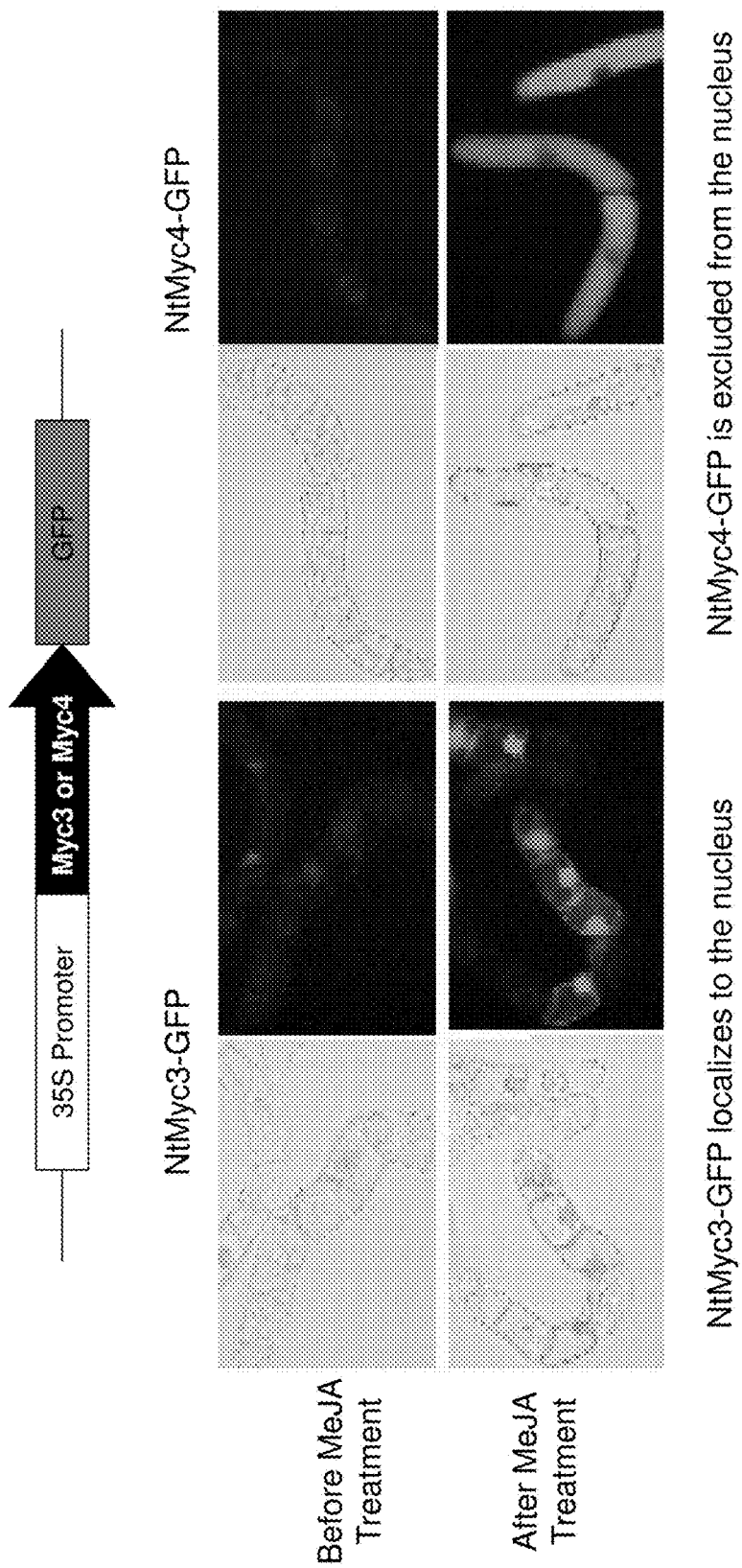
FIG. 10 shows differential localization of Myc3 and Myc4, respectively, in BY-2 cells after MeJA exposure. NtMyc3-GFP localized to the nucleus after MeJA exposure. In contrast, NtMyc4-GFP was excluded from the nucleus after MeJA exposure.

PMT promoter activation is responsive to various endogenous and exogenous signals, including phytohormones, wounding, and invasion by pathogens or insects. FIG. 1 illustrates the existence of multiple signal transduction pathways inducible by various phytohormones, including jasmonic acid ("JA"), auxin, and ethylene, which can affect PMT promoter activation. As shown in FIG. 1, the transcriptional regulation of PMT genes can be responsive to multiple signal transduction pathways that can be co-induced if multiple stimulants exist simultaneously in an environment. When a particular signal transduction pathway is induced, the expression level and/or the transcriptional activity of a transcriptional factor can be increased. Alternatively, the expression level and/or the transcriptional activity of a transcriptional factor can be decreased by inducing a particular signal transduction pathway. For example, a JA-inducible signal transduction pathway can be blocked by co-exposure to sufficient concentrations of auxin and/or ethylene that appear to have antagonistic effects on the JA-inducible pathway. In particular, PMT promoter activation induced by JA exposure can be blocked by exposure to auxin and/or ethylene.

In various plants, such as tobacco, the phytohormone jasmonic acid ("JA") (3-oxo-2-(cis-2-pentenyl)-1-cyclopentaneacetic acid) and/or its methylated ester derivative ("MeJA") can be utilized for inducing nicotine production. JA and/or MeJA can be utilized for inducing the expression of genes involved in the biosynthesis of secondary metabolites such as alkaloids, flavonoids, and terpenoids. Furthermore, JA and/or MeJA can be utilized to control various processes that regulate plant growth and environmental adaptation, including seed germination, regulation of carbon and nitrogen storage, photosynthesis, senescence, pollen development, fruit ripening, wound responses, and resistance to insects and pathogens. For regulating defense responses, JA and/or MeJA can be utilized to act synergistically with, or antagonistically against, two other plant hormones, salicylic acid (SA) and ethylene. JA and/or MeJA can be utilized for inducing the expression of genes encoding proteinase inhibitors involved in pest resistance and genes encoding defensins that exhibit antimicrobial activity. Therefore, various wound-induced and stress-induced biological responses of interest can be elicited by controlling the amount and extent of exposure to such phytohormones.

In *Nicotiana tabacum*, at least five PMT genes have been characterized: NtPMT1a, NtPMT1b, NtPMT2, NtPMT3, and NtPMT4. PMT gene expression in the roots of *N. tabacum* can be up-regulated by various stimuli, including topping procedures, the physical invasion by insects and/or other herbivores, and JA or MeJA exposure.

This disclosure describes a regulatory region upstream of the core promoter elements of PMT promoters, referred to as the "GAG motif," that confers PMT promoters with responsiveness to JA and MeJA. The GAG motif comprises a G-box like element, an AT-rich element, and a GCC-like box element. The GAG motif functions optimally as an intact, tripartite unit, in that the three elements must be utilized together, and must be arranged so that the G-box like element is positioned upstream of the AT-rich element, which is positioned upstream of the GCC-like box element.

Based on experimental studies described herein, the GAG and the G-G derivative fragment (similar to the structure of the GAG motif but deficient in the AT-rich element) have been shown to be responsive to JA and MeJA when plants are exposed to these phytohormones. The JA and MeJA responsiveness of the GAG motif can be mediated by members of the ERF and Myc families of transcriptional factors, as described herein. The GAG motif confers the recruitment of ERF and Myc transcriptional factors and other transcriptional factors when operably-linked to a promoter of interest, which is operably-linked to a transgene of interest positioned downstream of the promoter of interest. Suitable transgenes include genes that encode various enzymes involved in the biosynthesis of alkaloids, nicotine, and flavonoids, for example.

The sub-elements of the GAG motif that can recruit particular members of the ERF and Myc families have been further characterized by results described herein. For example, the experimental results show that ERF2/ERF3/ERF5 are recruited to the GAG motif in a JA-inducible manner. This occurs through the GCC-like box element and requires some or all of the AT-rich element for recruitment. For example, the experimental results show that the G-box element can recruit NtMyc3/NtMyc4 in a JA-inducible manner.

For up-regulating or down-regulating various promoters of interest, the following compositions and methods are contemplated:

In general, various embodiments are directed to expression vectors that enable the over-expression of transcriptional factors, NtMyc3, NtMyc4, NtERF2, and/or NtERF5, for modulating the production levels of nicotine, other alkaloids, including various flavonoids. These expression vectors can be transiently introduced into host plant cells or stably integrated into the genomes of host plant cells to generate transgenic plants by various methods known to persons skilled in the art. When these expression vectors are stably integrated into the genomes of host plant cells to generate stable cell lines or transgenic plants, the over-expression of transcriptional factors, NtMyc3, NtMyc4, NtERF2, and/or NtERF5, can be utilized as a method for modulating the promoter activation of endogenous promoters that are responsive to these transcriptional factors. Furthermore, such host plant cells can be further manipulated to receive heterologous promoter constructs that are responsive to transcriptional factors, NtMyc3, NtMyc4, NtERF2, and/or NtERF5. Furthermore, such host plant cells can be further manipulated to receive heterologous promoter constructs that have been modified by incorporating one or more GAG motifs upstream of the core elements of the heterologous promoter of interest.

Any promoter of interest can be manipulated to be responsive to JA and MeJA by incorporating one or more GAG motifs and/or derivative GAG motifs upstream of the promoter of interest. Suitable promoters include various promoters of any origin that can be activated by the transcriptional machinery of plant cells, such as various homologous or heterologous plant promoters and various promoters derived from plant pathogens, including bacteria and viruses. Suitable promoters include constitutively active promoters and inducible promoters.

For various expression vectors described below, various genes that encode enzymes involved in biosynthetic pathways for the production of alkaloids, flavonoids, and nicotine can be suitable as transgenes that can be operably-linked to a promoter of interest.

In another embodiment, an expression vector comprises a promoter operably-linked to the cDNA encoding Myc3, Myc4, ERF2, and/or ERF5. In another embodiment, a plant cell line comprises an expression vector comprising a promoter operably-linked to the cDNA encoding Myc3, Myc4, ERF2, and/or ERF5. In another embodiment, a transgenic plant comprises an expression vector comprising a promoter operably-linked to the cDNA encoding Myc3, Myc4, ERF2, and/or ERF5. In another embodiment, methods for genetically modulating the production of alkaloids, flavonoids, and nicotine are provided, comprising: introducing an expression vector comprising a promoter operably-linked to the cDNA encoding Myc3, Myc4, ERF2, and/or ERF5.

In another embodiment, an expression vector comprises a first promoter operably-linked to cDNA encoding Myc3, Myc4, ERF2, and/or ERF5; and a second promoter operably-linked to cDNA encoding an enzyme involved in the biosynthesis of alkaloids. In another embodiment, a plant cell line comprises an expression vector comprising a first promoter operably-linked to cDNA encoding Myc3, Myc4, ERF2, and/or ERF5; and a second promoter operably-linked to cDNA encoding an enzyme involved in the biosynthesis of alkaloids. In another embodiment, a transgenic plant comprises an expression vector comprising a first promoter operably-linked to cDNA encoding Myc3, Myc4, ERF2, and/or ERF5; and a second promoter operably-linked to cDNA encoding an enzyme involved in the biosynthesis of alkaloids. In another embodiment, methods for genetically modulating the production level of alkaloids are provided, comprising: introducing an expression vector comprising a first promoter operably-linked to cDNA encoding Myc3, Myc4, ERF2, and/or ERF5; and a second promoter operably-linked to cDNA encoding an enzyme involved in the biosynthesis of alkaloids.

In another embodiment, an expression vector comprises a first promoter operably-linked to cDNA encoding Myc3, Myc4, ERF2, and/or ERF5; and a second promoter operably-linked to cDNA encoding an enzyme involved in the biosynthesis of flavonoids. In another embodiment, a plant cell line comprises an expression vector comprising a first promoter operably-linked to cDNA encoding Myc3, Myc4, ERF2, and/or ERF5; and a second promoter operably-linked to cDNA encoding an enzyme involved in the biosynthesis of flavonoids. In another embodiment, a transgenic plant comprises an expression vector comprising a first promoter operably-linked to cDNA encoding Myc3, Myc4, ERF2, and/or ERF5; and a second promoter operably-linked to cDNA encoding an enzyme involved in the biosynthesis of flavonoids. In another embodiment, methods for modulating the production level of flavonoids are provided, comprising: introducing an expression vector comprising a first promoter operably-linked to cDNA encoding Myc3, Myc4, ERF2, and/or ERF5; and a second promoter operably-linked to cDNA encoding an enzyme involved in the biosynthesis of flavonoids.

In another embodiment, an expression vector comprises a first promoter operably-linked to cDNA encoding Myc3, Myc4, ERF2, and/or ERF5; and a second promoter operably-linked to cDNA encoding an enzyme involved in nicotine biosynthesis. In another embodiment, a plant cell line comprises an expression vector comprising a first promoter operably-linked to cDNA encoding Myc3, Myc4, ERF2, and/or ERF5; and a second promoter operably-linked to cDNA encoding an enzyme involved in nicotine biosynthesis. In another embodiment, a transgenic plant comprises an expression vector comprising a first promoter operably-linked to cDNA encoding Myc3, Myc4, ERF2, and/or ERF5; and a second promoter operably-linked to cDNA encoding an enzyme involved in nicotine biosynthesis. In a preferred embodiment, the enzyme is PMT involved in nicotine biosynthesis. In another embodiment, methods for genetically modulating the production level of nicotine are provided, comprising: introducing an expression vector comprising a first promoter operably-linked to cDNA encoding Myc3, Myc4, ERF2, and/or ERF5; and a second promoter operably-linked to cDNA encoding an enzyme involved in nicotine biosynthesis. FIG. 11 shows the polynucleotide sequence for NtMyc3 cDNA (SEQ ID NO:1). FIG. 12 shows the polypeptide sequence for NtMyc3 protein (SEQ ID NO:2). FIG. 13 shows the polynucleotide sequence for NtMyc4 cDNA (SEQ ID NO:3). FIG. 14 shows the polypeptide sequence for NtMyc4 protein (SEQ ID NO:4). FIG. 15 shows the polynucleotide sequence for NtERF2 cDNA (SEQ ID NO:5), which encodes for Ethylene-responsive transcription factor 2 (Swiss Protein Accession No. Q40479; Plant Cell 7 (2), p173-182 (1995; PUBMED #7756828). FIG. 16 shows the polynucleotide sequence for NtERF5 cDNA (SEQ ID NO:6), which encodes ERF Transcription Factor 5 (NCBI Accession No. AY655738; Mol. Plant Microbe Interact. 17(10), p1162-1171 (2004); PUBMED #15497409). NtERF5 cDNA (SEQ ID NO:6) also refers to sequence published in Mol. Plant Microbe Interact. 17(10), p1162-1171 (2004).

Another embodiment is directed to an isolated cDNA encoding NtMyc3 (SEQ ID NO:1), or fragments thereof. Another embodiment is directed to an isolated cDNA encoding NtMyc3 and having at least 85%, 90%, 95%, 96%, 97%, 98%, and 99% sequence identity to SEQ ID NO:1, or variant fragments thereof.

Another embodiment is directed to an isolated cDNA encoding NtMyc4 (SEQ ID NO:3), or fragments thereof. Another embodiment is directed to an isolated cDNA encoding NtMyc4 and having at least 85%, 90%, 95%, 96%, 97%, 98%, and 99% sequence identity to SEQ ID NO:3, or variant fragments thereof.

Another embodiment is directed to an isolated polypeptide NtMyc3 (SEQ ID NO:2), or fragments thereof. Another embodiment is directed to an isolated polypeptide NtMyc3 and having at least 85%, 90%, 95%, 96%, 97%, 98%, and 99% sequence identity to SEQ ID NO:2, or fragments thereof.

Another embodiment is directed to an isolated polypeptide NtMyc4 (SEQ ID NO:4), or fragments thereof. Another embodiment is directed to an isolated polypeptide NtMyc4 and having at least 85%, 90%, 95%, 96%, 97%, 98%, and 99% sequence identity to SEQ ID NO:4, or variant fragments thereof.

Another embodiment is directed to an expression vector comprising an isolated cDNA encoding NtMyc3 (SEQ ID NO:1), or fragments thereof. Another embodiment is directed to an expression vector comprising an isolated cDNA encoding NtMyc3 and having at least 85%, 90%, 95%, 96%, 97%, 98%, and 99% sequence identity to SEQ ID NO:1, or fragments thereof.

Another embodiment is directed to an expression vector comprising an isolated cDNA encoding NtMyc4 (SEQ ID NO:3), or fragments thereof. Another embodiment is directed to an expression vector comprising an isolated cDNA encoding NtMyc4 and having at least 85%, 90%, 95%, 96%, 97%, 98%, and 99% sequence identity to SEQ ID NO:3, or fragments thereof.

Another embodiment is directed to an expression vector comprising an isolated cDNA encoding NtMyc3 and having at least 85%, 90%, 95%, 96%, 97%, 98%, and 99% sequence identity to SEQ ID NO:1, or fragments thereof; and an isolated cDNA encoding NtMyc4 and having at least 85%, 90%, 95%, 96%, 97%, 98%, and 99% sequence identity to SEQ ID NO:3, or fragments thereof.

Another embodiment is directed to an expression vector comprising cDNA encoding a Myc transcriptional factor and/or cDNA encoding a ERF transcriptional factor. In particular, this embodiment is directed to an expression vector comprising: a first sequence comprising an isolated cDNA encoding NtMyc3 and having at least 85%, 90%, 95%, 96%, 97%, 98%, and 99% sequence identity to SEQ ID NO:1, or fragments thereof; and/or a second sequence comprising an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO:5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5.

Another embodiment is directed to a plant cell line comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof.

Another embodiment is directed to a plant cell line comprising an expression vector comprising at least one ERF transcriptional factor and at least one Myc transcriptional factor. In particular, this embodiment is directed to a plant cell line comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO:5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5.

Another embodiment is directed to a transgenic plant comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof. In a preferred embodiment, the transgenic plant is a tobacco plant.

Another embodiment is directed to a transgenic plant comprising an expression vector comprising at least one Myc transcriptional factor and at least one ERF transcriptional factor. Another embodiment is directed to a transgenic plant comprising an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO:5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5. In a preferred embodiment, the transgenic plant is a tobacco plant.

Another embodiment is directed to a method for genetically regulating nicotine levels in plants, comprising introducing into a plant an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof. In a preferred embodiment, the transgenic plant is a tobacco plant.

Another embodiment is directed to a method for genetically regulating nicotine levels in plants, comprising introducing into a plant an expression vector comprising an isolated cDNA encoding NtMyc3 and having at least 85%, 90%, 95%, 96%, 97%, 98%, and 99% sequence identity to SEQ ID NO:1, or fragments thereof; and/or an isolated cDNA encoding NtMyc4 and having at least 85%, 90%, 95%, 96%, 97%, 98%, and 99% sequence identity to SEQ ID NO:3, or fragments thereof; and an isolated cDNA encoding NtERF2 and having at least 85%, 90%, 95%, 96%, 97%, 98%, and 99% sequence identity to SEQ ID NO:5, or fragments thereof; and/or an isolated cDNA encoding NtERF5 and having at least 85%, 90%, 95%, 96%, 97%, 98%, and 99% sequence identity to SEQ ID NO:6, or fragments thereof, wherein the SEQ ID NO:5 represents the cDNA sequence encoding NtERF2, and the SEQ ID NO:6 represents the cDNA sequence encoding NtERF5. In a preferred embodiment, the transgenic plant is a tobacco plant. In a preferred embodiment, the nicotine level in the genetically-modified plant is increased. In another preferred embodiment, the nicotine level in the genetically-modified plant is decreased.

Various embodiments are directed to seeds derived from genetically-modified transgenic plants described herein.

Various embodiments are directed to various polynucleotide molecules that can suppress the expression levels of genes involved in the biosynthetic pathways for the production of alkaloids, flavonoids, and nicotine. Examples of suitable compositions include ERF and Myc anti-sense polynucleotides that are complementary to ERF and Myc transcript sequences, such as RNAi molecules, microRNAs, and other dominant negative constructs known to persons skilled in the art.

It will be appreciated that, although specific embodiments of the invention have been described herein for purposes of illustration, various modifications may be made without departing from the spirit and scope of the invention. Accordingly, the invention is not limited except as by the appended claims.

We claim:

1. A nucleic acid molecule comprising a polynucleotide having at least 95% sequence identity to the nucleotide sequence of SEQ ID NO:3 and a heterologous promoter operably linked to said polynucleotide.

2. The nucleic acid molecule of claim 1, comprising the nucleotide sequence of SEQ ID NO:3.

3. An expression vector comprising the nucleic acid molecule of claim 1.

4. A tobacco plant cell comprising the expression vector of claim 3.

5. A tobacco plant comprising the tobacco plant cell of claim 4.

6. The nucleic acid molecule of claim 1, comprising a nucleotide sequence having at least 98% sequence identity to SEQ ID NO:3.

* * * * *

SEQUENCE LISTING

<160> NUMBER OF SEQ ID NOS: 10

<210> SEQ ID NO 1
<211> LENGTH: 2040
<212> TYPE: DNA
<213> ORGANISM: Nicotiana tabacum
<220> FEATURE:
<221> NAME/KEY: CDS
<222> LOCATION: (1)..(2040)

<400> SEQUENCE: 1

| | | | | | | | | | | | | | | | | |
|---|---|---|---|---|---|---|---|---|---|---|---|---|---|---|---|---|
| atg | act | gat | tac | agc | tta | ccc | acc | atg | aat | ttg | tgg | aat | act | agt | ggt | 48 |
| Met | Thr | Asp | Tyr | Ser | Leu | Pro | Thr | Met | Asn | Leu | Trp | Asn | Thr | Ser | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| act | acc | gat | gac | aac | gtt | tct | atg | atg | gaa | tct | ttt | atg | tct | tct | gat | 96 |
| Thr | Thr | Asp | Asp | Asn | Val | Ser | Met | Met | Glu | Ser | Phe | Met | Ser | Ser | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| ctc | act | tca | ttt | tgg | gct | act | tct | aat | tct | act | act | gct | gct | gtt | acc | 144 |
| Leu | Thr | Ser | Phe | Trp | Ala | Thr | Ser | Asn | Ser | Thr | Thr | Ala | Ala | Val | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| tct | aat | tct | aat | ctt | att | cca | gtt | aat | acc | cta | act | gtt | ctt | ctt | ccg | 192 |
| Ser | Asn | Ser | Asn | Leu | Ile | Pro | Val | Asn | Thr | Leu | Thr | Val | Leu | Leu | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| tct | tct | tgt | gct | tct | act | gtc | aca | gct | gtg | gct | gtc | gat | gct | tca | aaa | 240 |
| Ser | Ser | Cys | Ala | Ser | Thr | Val | Thr | Ala | Val | Ala | Val | Asp | Ala | Ser | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tcc | atg | tct | ttt | ttc | aac | caa | gaa | act | ctt | cag | cag | cgt | ctt | caa | acc | 288 |
| Ser | Met | Ser | Phe | Phe | Asn | Gln | Glu | Thr | Leu | Gln | Gln | Arg | Leu | Gln | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| ctc | att | gat | ggt | gct | cgt | gag | acg | tgg | acc | tat | gcc | atc | ttt | tgg | cag | 336 |
| Leu | Ile | Asp | Gly | Ala | Arg | Glu | Thr | Trp | Thr | Tyr | Ala | Ile | Phe | Trp | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| tca | tcc | gtc | gtt | gat | tta | tcg | agt | ccg | ttt | gtg | ttg | ggc | tgg | gga | gat | 384 |
| Ser | Ser | Val | Val | Asp | Leu | Ser | Ser | Pro | Phe | Val | Leu | Gly | Trp | Gly | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| ggt | tac | tac | aaa | ggt | gaa | gaa | gat | aaa | gcc | aat | agg | aaa | tta | gct | gtt | 432 |
| Gly | Tyr | Tyr | Lys | Gly | Glu | Glu | Asp | Lys | Ala | Asn | Arg | Lys | Leu | Ala | Val | |
| | 130 | | | | | 135 | | | | | 140 | | | | | |

| | | | | | | | | | | | | | | | | |
|---|---|---|---|---|---|---|---|---|---|---|---|---|---|---|---|---|
| tct | tct | cct | gct | tat | att | gct | gag | caa | gaa | cac | cga | aaa | aag | gtt | ctc | 480 |
| Ser | Ser | Pro | Ala | Tyr | Ile | Ala | Glu | Gln | Glu | His | Arg | Lys | Lys | Val | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cgg | gag | ctg | aat | tcg | ttg | atc | tcc | ggc | acg | caa | acc | ggc | act | gat | gat | 528 |
| Arg | Glu | Leu | Asn | Ser | Leu | Ile | Ser | Gly | Thr | Gln | Thr | Gly | Thr | Asp | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| gcc | gtc | gat | gaa | gaa | gtt | acc | gac | act | gaa | tgg | ttc | ttc | ctt | att | tcc | 576 |
| Ala | Val | Asp | Glu | Glu | Val | Thr | Asp | Thr | Glu | Trp | Phe | Phe | Leu | Ile | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| atg | acc | caa | tcg | ttt | gtt | aac | gga | agt | ggg | ctt | ccg | ggt | cag | gcc | tta | 624 |
| Met | Thr | Gln | Ser | Phe | Val | Asn | Gly | Ser | Gly | Leu | Pro | Gly | Gln | Ala | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| tac | aat | tcc | agc | cct | att | tgg | gtc | gcc | gga | gca | gag | aaa | ttg | gca | gct | 672 |
| Tyr | Asn | Ser | Ser | Pro | Ile | Trp | Val | Ala | Gly | Ala | Glu | Lys | Leu | Ala | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| tcc | cac | tgc | gaa | cgg | gct | cgg | cag | gcc | cag | gga | ttc | ggg | ctt | cag | acg | 720 |
| Ser | His | Cys | Glu | Arg | Ala | Arg | Gln | Ala | Gln | Gly | Phe | Gly | Leu | Gln | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atg | gtt | tgt | att | cct | tca | gca | aac | ggc | gtg | gtt | gaa | ttg | ggc | tcc | acg | 768 |
| Met | Val | Cys | Ile | Pro | Ser | Ala | Asn | Gly | Val | Val | Glu | Leu | Gly | Ser | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| gag | ttg | ata | atc | cag | agt | tgt | gat | ctc | atg | aac | aag | gtt | aga | gta | ttg | 816 |
| Glu | Leu | Ile | Ile | Gln | Ser | Cys | Asp | Leu | Met | Asn | Lys | Val | Arg | Val | Leu | |

-continued

|  | 260 |  |  |  | 265 |  |  |  | 270 |  |  |  |  |  |  |
|---|---|---|---|---|---|---|---|---|---|---|---|---|---|---|---|
| ttt | aac | ttc | aat | aat | gat | ttg | ggc | tct | ggt | tcg | tgg | gct | gtg | cag | ccc | 864 |
| Phe | Asn | Phe | Asn | Asn | Asp | Leu | Gly | Ser | Gly | Ser | Trp | Ala | Val | Gln | Pro | |
|  |  | 275 |  |  |  | 280 |  |  |  | 285 |  |  |  |  |  |  |
| gag | agc | gat | ccg | tcc | gct | ctt | tgg | ctc | act | gat | cca | tcg | tct | gca | gct | 912 |
| Glu | Ser | Asp | Pro | Ser | Ala | Leu | Trp | Leu | Thr | Asp | Pro | Ser | Ser | Ala | Ala | |
|  | 290 |  |  |  |  | 295 |  |  |  |  | 300 |  |  |  |  |  |
| gta | gaa | gtc | caa | gat | tta | aat | aca | gtt | aag | gca | aat | tca | gtt | cca | tca | 960 |
| Val | Glu | Val | Gln | Asp | Leu | Asn | Thr | Val | Lys | Ala | Asn | Ser | Val | Pro | Ser | |
| 305 |  |  |  |  | 310 |  |  |  |  | 315 |  |  |  |  | 320 |  |
| agt | aat | agt | agt | aag | caa | gtt | gtg | ttt | gat | aat | gag | aat | aat | ggt | cac | 1008 |
| Ser | Asn | Ser | Ser | Lys | Gln | Val | Val | Phe | Asp | Asn | Glu | Asn | Asn | Gly | His | |
|  |  |  |  | 325 |  |  |  |  | 330 |  |  |  |  | 335 |  |  |
| agt | tct | gat | aat | cag | caa | cag | cag | cat | tct | aag | cat | gaa | aca | caa | gga | 1056 |
| Ser | Ser | Asp | Asn | Gln | Gln | Gln | Gln | His | Ser | Lys | His | Glu | Thr | Gln | Gly | |
|  |  |  | 340 |  |  |  |  | 345 |  |  |  |  | 350 |  |  |  |
| ttt | ttc | aca | agg | gag | ttg | aat | ttt | tca | gaa | ttt | ggg | ttt | gat | gga | agt | 1104 |
| Phe | Phe | Thr | Arg | Glu | Leu | Asn | Phe | Ser | Glu | Phe | Gly | Phe | Asp | Gly | Ser | |
|  |  | 355 |  |  |  |  | 360 |  |  |  |  | 365 |  |  |  |  |
| agt | aat | aat | agg | aat | ggg | aat | tca | tca | ctt | tct | tgc | aag | cca | gag | tcg | 1152 |
| Ser | Asn | Asn | Arg | Asn | Gly | Asn | Ser | Ser | Leu | Ser | Cys | Lys | Pro | Glu | Ser | |
| 370 |  |  |  |  | 375 |  |  |  |  | 380 |  |  |  |  |  |  |
| ggg | gaa | atc | ttg | aat | ttt | ggt | gat | agt | act | aag | aaa | agt | gca | aat | ggg | 1200 |
| Gly | Glu | Ile | Leu | Asn | Phe | Gly | Asp | Ser | Thr | Lys | Lys | Ser | Ala | Asn | Gly | |
| 385 |  |  |  |  | 390 |  |  |  |  | 395 |  |  |  |  | 400 |  |
| aac | tta | ttt | tcg | ggt | cag | tcc | cat | ttt | ggg | gca | ggg | gag | gag | aat | aag | 1248 |
| Asn | Leu | Phe | Ser | Gly | Gln | Ser | His | Phe | Gly | Ala | Gly | Glu | Glu | Asn | Lys | |
|  |  |  | 405 |  |  |  |  | 410 |  |  |  |  | 415 |  |  |  |
| aac | aag | aaa | agg | tca | cct | gct | tcc | aga | gga | agc | aat | gaa | gaa | gga | atg | 1296 |
| Asn | Lys | Lys | Arg | Ser | Pro | Ala | Ser | Arg | Gly | Ser | Asn | Glu | Glu | Gly | Met | |
|  |  | 420 |  |  |  |  | 425 |  |  |  |  | 430 |  |  |  |  |
| ctt | tca | ttt | gtt | tcg | ggt | aca | atc | ttg | cct | gca | gct | tct | ggt | gcg | atg | 1344 |
| Leu | Ser | Phe | Val | Ser | Gly | Thr | Ile | Leu | Pro | Ala | Ala | Ser | Gly | Ala | Met | |
|  | 435 |  |  |  |  | 440 |  |  |  |  | 445 |  |  |  |  |  |
| aag | tca | agt | gga | ggt | gta | ggt | gaa | gac | tct | gat | cat | tcg | gat | ctt | gag | 1392 |
| Lys | Ser | Ser | Gly | Gly | Val | Gly | Glu | Asp | Ser | Asp | His | Ser | Asp | Leu | Glu | |
| 450 |  |  |  |  | 455 |  |  |  |  | 460 |  |  |  |  |  |  |
| gcc | tca | gtg | gtg | aaa | gaa | gct | gaa | agt | agt | aga | gtt | gta | gaa | ccc | gaa | 1440 |
| Ala | Ser | Val | Val | Lys | Glu | Ala | Glu | Ser | Ser | Arg | Val | Val | Glu | Pro | Glu | |
| 465 |  |  |  |  | 470 |  |  |  |  | 475 |  |  |  |  | 480 |  |
| aag | agg | cca | aag | aag | cga | gga | agg | aag | cca | gca | aat | gga | cgg | gag | gaa | 1488 |
| Lys | Arg | Pro | Lys | Lys | Arg | Gly | Arg | Lys | Pro | Ala | Asn | Gly | Arg | Glu | Glu | |
|  |  |  |  | 485 |  |  |  |  | 490 |  |  |  |  | 495 |  |  |
| cct | ttg | aat | cac | gtc | gaa | gca | gag | agg | caa | agg | aga | gag | aaa | tta | aac | 1536 |
| Pro | Leu | Asn | His | Val | Glu | Ala | Glu | Arg | Gln | Arg | Arg | Glu | Lys | Leu | Asn | |
|  |  |  | 500 |  |  |  |  | 505 |  |  |  |  | 510 |  |  |  |
| caa | agg | ttc | tac | gca | tta | aga | gct | gtt | gtt | ccg | aat | gtg | tcc | aag | atg | 1584 |
| Gln | Arg | Phe | Tyr | Ala | Leu | Arg | Ala | Val | Val | Pro | Asn | Val | Ser | Lys | Met | |
|  |  | 515 |  |  |  |  | 520 |  |  |  |  | 525 |  |  |  |  |
| gac | aag | gca | tca | ctg | ctt | gga | gat | gca | att | tca | tat | att | aat | gag | ctg | 1632 |
| Asp | Lys | Ala | Ser | Leu | Leu | Gly | Asp | Ala | Ile | Ser | Tyr | Ile | Asn | Glu | Leu | |
|  | 530 |  |  |  |  | 535 |  |  |  |  | 540 |  |  |  |  |  |
| aag | ttg | aag | ctt | caa | aat | aca | gaa | aca | gat | aga | gaa | gaa | ttg | aag | agc | 1680 |
| Lys | Leu | Lys | Leu | Gln | Asn | Thr | Glu | Thr | Asp | Arg | Glu | Glu | Leu | Lys | Ser | |
| 545 |  |  |  |  | 550 |  |  |  |  | 555 |  |  |  |  | 560 |  |
| caa | ata | gaa | gat | tta | aag | aaa | gaa | tta | gtt | agt | aaa | gac | tca | agg | cgc | 1728 |
| Gln | Ile | Glu | Asp | Leu | Lys | Lys | Glu | Leu | Val | Ser | Lys | Asp | Ser | Arg | Arg | |
|  |  |  |  | 565 |  |  |  |  | 570 |  |  |  |  | 575 |  |  |
| cct | ggt | cct | cca | cca | tca | aat | cat | gat | cac | aag | atg | tct | agc | cat | act | 1776 |

```
                Pro Gly Pro Pro Pro Ser Asn His Asp His Lys Met Ser Ser His Thr
                                580                 585                 590 gga agc aag att gta gac gtg gat ata gat gtt aag ata att gga tgg            1824
Gly Ser Lys Ile Val Asp Val Asp Ile Asp Val Lys Ile Ile Gly Trp
        595                 600                 605 gat gcg atg att cgt ata caa tgt aat aaa aag aat cat cca gct gca            1872
Asp Ala Met Ile Arg Ile Gln Cys Asn Lys Lys Asn His Pro Ala Ala
610                 615                 620 agg tta atg gta gcc ctc aag gag tta gat cta gat gtg cac cat gcc            1920
Arg Leu Met Val Ala Leu Lys Glu Leu Asp Leu Asp Val His His Ala
625                 630                 635                 640 agt gtt tca gtg gtg aac gat ttg atg atc caa caa gcc act gtg aaa            1968
Ser Val Ser Val Val Asn Asp Leu Met Ile Gln Gln Ala Thr Val Lys
                645                 650                 655 atg ggt agc aga ctt tac acg gaa gag caa ctt agg ata gca ttg aca            2016
Met Gly Ser Arg Leu Tyr Thr Glu Glu Gln Leu Arg Ile Ala Leu Thr
            660                 665                 670 tcc aga gtt gct gaa aca cgc taa                                            2040
Ser Arg Val Ala Glu Thr Arg
        675

<210> SEQ ID NO 2
<211> LENGTH: 679
<212> TYPE: PRT
<213> ORGANISM: Nicotiana tabacum

<400> SEQUENCE: 2

Met Thr Asp Tyr Ser Leu Pro Thr Met Asn Leu Trp Asn Thr Ser Gly
1               5                   10                  15

Thr Thr Asp Asp Asn Val Ser Met Met Glu Ser Phe Met Ser Ser Asp
                20                  25                  30

Leu Thr Ser Phe Trp Ala Thr Ser Asn Ser Thr Thr Ala Ala Val Thr
            35                  40                  45

Ser Asn Ser Asn Leu Ile Pro Val Asn Thr Leu Thr Val Leu Leu Pro
        50                  55                  60

Ser Ser Cys Ala Ser Thr Val Thr Ala Ala Val Asp Ala Ser Lys
65                  70                  75                  80

Ser Met Ser Phe Phe Asn Gln Glu Thr Leu Gln Gln Arg Leu Gln Thr
                85                  90                  95

Leu Ile Asp Gly Ala Arg Glu Thr Trp Thr Tyr Ala Ile Phe Trp Gln
            100                 105                 110

Ser Ser Val Val Asp Leu Ser Ser Pro Phe Val Leu Gly Trp Gly Asp
        115                 120                 125

Gly Tyr Tyr Lys Gly Glu Glu Asp Lys Ala Asn Arg Lys Leu Ala Val
    130                 135                 140

Ser Ser Pro Ala Tyr Ile Ala Glu Gln Glu His Arg Lys Lys Val Leu
145                 150                 155                 160

Arg Glu Leu Asn Ser Leu Ile Ser Gly Thr Gln Thr Gly Thr Asp Asp
                165                 170                 175

Ala Val Asp Glu Glu Val Thr Asp Thr Glu Trp Phe Phe Leu Ile Ser
            180                 185                 190

Met Thr Gln Ser Phe Val Asn Gly Ser Gly Leu Pro Gly Gln Ala Leu
        195                 200                 205

Tyr Asn Ser Ser Pro Ile Trp Val Ala Gly Ala Glu Lys Leu Ala Ala
    210                 215                 220

Ser His Cys Glu Arg Ala Arg Gln Ala Gln Gly Phe Gly Leu Gln Thr
225                 230                 235                 240
```

```
Met Val Cys Ile Pro Ser Ala Asn Gly Val Glu Leu Gly Ser Thr
                    245                 250                 255

Glu Leu Ile Ile Gln Ser Cys Asp Leu Met Asn Lys Val Arg Val Leu
                    260                 265                 270

Phe Asn Phe Asn Asn Asp Leu Gly Ser Gly Ser Trp Ala Val Gln Pro
                275                 280                 285

Glu Ser Asp Pro Ser Ala Leu Trp Leu Thr Asp Pro Ser Ser Ala Ala
            290                 295                 300

Val Glu Val Gln Asp Leu Asn Thr Val Lys Ala Asn Ser Val Pro Ser
305                 310                 315                 320

Ser Asn Ser Ser Lys Gln Val Val Phe Asp Asn Glu Asn Asn Gly His
                325                 330                 335

Ser Ser Asp Asn Gln Gln Gln Gln His Ser Lys His Glu Thr Gln Gly
                340                 345                 350

Phe Phe Thr Arg Glu Leu Asn Phe Ser Glu Phe Gly Phe Asp Gly Ser
                355                 360                 365

Ser Asn Asn Arg Asn Gly Asn Ser Ser Leu Ser Cys Lys Pro Glu Ser
        370                 375                 380

Gly Glu Ile Leu Asn Phe Gly Asp Ser Thr Lys Lys Ser Ala Asn Gly
385                 390                 395                 400

Asn Leu Phe Ser Gly Gln Ser His Phe Gly Ala Gly Glu Glu Asn Lys
                405                 410                 415

Asn Lys Lys Arg Ser Pro Ala Ser Arg Gly Ser Asn Glu Glu Gly Met
                420                 425                 430

Leu Ser Phe Val Ser Gly Thr Ile Leu Pro Ala Ala Ser Gly Ala Met
            435                 440                 445

Lys Ser Ser Gly Gly Val Gly Glu Asp Ser Asp His Ser Asp Leu Glu
        450                 455                 460

Ala Ser Val Val Lys Glu Ala Glu Ser Ser Arg Val Val Glu Pro Glu
465                 470                 475                 480

Lys Arg Pro Lys Lys Arg Gly Arg Lys Pro Ala Asn Gly Arg Glu Glu
                485                 490                 495

Pro Leu Asn His Val Glu Ala Glu Arg Gln Arg Arg Glu Lys Leu Asn
                500                 505                 510

Gln Arg Phe Tyr Ala Leu Arg Ala Val Val Pro Asn Val Ser Lys Met
            515                 520                 525

Asp Lys Ala Ser Leu Leu Gly Asp Ala Ile Ser Tyr Ile Asn Glu Leu
        530                 535                 540

Lys Leu Lys Leu Gln Asn Thr Glu Thr Asp Arg Glu Glu Leu Lys Ser
545                 550                 555                 560

Gln Ile Glu Asp Leu Lys Lys Glu Leu Val Ser Lys Asp Ser Arg Arg
                565                 570                 575

Pro Gly Pro Pro Pro Ser Asn His Asp His Lys Met Ser Ser His Thr
                580                 585                 590

Gly Ser Lys Ile Val Asp Val Asp Ile Asp Val Lys Ile Ile Gly Trp
            595                 600                 605

Asp Ala Met Ile Arg Ile Gln Cys Asn Lys Lys Asn His Pro Ala Ala
        610                 615                 620

Arg Leu Met Val Ala Leu Lys Glu Leu Asp Leu Asp Val His His Ala
625                 630                 635                 640

Ser Val Ser Val Val Asn Asp Leu Met Ile Gln Gln Ala Thr Val Lys
                645                 650                 655
```

```
Met Gly Ser Arg Leu Tyr Thr Glu Glu Gln Leu Arg Ile Ala Leu Thr
            660                 665                 670

Ser Arg Val Ala Glu Thr Arg
        675

<210> SEQ ID NO 3
<211> LENGTH: 2046
<212> TYPE: DNA
<213> ORGANISM: Nicotiana tabacum
<220> FEATURE:
<221> NAME/KEY: CDS
<222> LOCATION: (1)..(2046)

<400> SEQUENCE: 3 atg act gat tac agc tta ccc acc atg aat ttg tgg aat act agt ggt      48
Met Thr Asp Tyr Ser Leu Pro Thr Met Asn Leu Trp Asn Thr Ser Gly
1               5                   10                  15 act acc gat gac aac gtt act atg atg gaa gct ttt atg tct tct gat      96
Thr Thr Asp Asp Asn Val Thr Met Met Glu Ala Phe Met Ser Ser Asp
                20                  25                  30 ctc act tca ttt tgg gct act tct aat tct act gct gtt gct gct gtt     144
Leu Thr Ser Phe Trp Ala Thr Ser Asn Ser Thr Ala Val Ala Ala Val
            35                  40                  45 acc tct aat tct aat cat att cca gtt aat acc cca acg gtt ctt ctt     192
Thr Ser Asn Ser Asn His Ile Pro Val Asn Thr Pro Thr Val Leu Leu
        50                  55                  60 ccg tct tct tgt gcc tct act gtc aca gct gtg gct gtc gat gct tca     240
Pro Ser Ser Cys Ala Ser Thr Val Thr Ala Val Ala Val Asp Ala Ser
65                  70                  75                  80 aaa tcc atg tct ttt ttc aac caa gaa acc ctt caa cag cgt ctt caa     288
Lys Ser Met Ser Phe Phe Asn Gln Glu Thr Leu Gln Gln Arg Leu Gln
                85                  90                  95 acg ctc att gat ggt gct cgt gag acg tgg acc tat gcc atc ttt tgg     336
Thr Leu Ile Asp Gly Ala Arg Glu Thr Trp Thr Tyr Ala Ile Phe Trp
            100                 105                 110 cag tca tcc gcc gtt gat tta acg agt ccg ttt gtg ttg ggc tgg gga     384
Gln Ser Ser Ala Val Asp Leu Thr Ser Pro Phe Val Leu Gly Trp Gly
        115                 120                 125 gat ggt tac tac aaa ggt gaa gaa gat aaa gcc aat agg aaa tta gct     432
Asp Gly Tyr Tyr Lys Gly Glu Glu Asp Lys Ala Asn Arg Lys Leu Ala
    130                 135                 140 gtt tct tct cct gct tat ata gct gag caa gaa cac cgg aaa aag gtt     480
Val Ser Ser Pro Ala Tyr Ile Ala Glu Gln Glu His Arg Lys Lys Val
145                 150                 155                 160 ctc cgg gag ctg aat tcg ttg att tcc ggc acg caa acc ggc act gat     528
Leu Arg Glu Leu Asn Ser Leu Ile Ser Gly Thr Gln Thr Gly Thr Asp
                165                 170                 175 gat gcc gtc gat gaa gaa gtt acc gac act gaa tgg ttc ttc ctt att     576
Asp Ala Val Asp Glu Glu Val Thr Asp Thr Glu Trp Phe Phe Leu Ile
            180                 185                 190 tcc atg acc cag tcg ttt gtt aac gga agt ggg ctt ccg ggt cag gcc     624
Ser Met Thr Gln Ser Phe Val Asn Gly Ser Gly Leu Pro Gly Gln Ala
        195                 200                 205 tta tac aat tcc agc cct att tgg gtc gcc gga gca gag aaa ttg gca     672
Leu Tyr Asn Ser Ser Pro Ile Trp Val Ala Gly Ala Glu Lys Leu Ala
    210                 215                 220 gct tcc cac tgc gaa cgg gct cgg cag gcc cag gga ttc ggg ctt cag     720
Ala Ser His Cys Glu Arg Ala Arg Gln Ala Gln Gly Phe Gly Leu Gln
225                 230                 235                 240 acg atg gtt tgt att cct tca gca aac ggc gtg gtt gaa ttg ggc tcc     768
Thr Met Val Cys Ile Pro Ser Ala Asn Gly Val Val Glu Leu Gly Ser
```

-continued

|     | 245 |     |     |     |     | 250 |     |     |     |     | 255 |     |     |     |     |      |
|-----|-----|-----|-----|-----|-----|-----|-----|-----|-----|-----|-----|-----|-----|-----|-----|------|
| acg | gag | ttg | att | att | cag | agt | tct | gat | ctc | atg | aac | aag | gtt | aga | gta | 816  |
| Thr | Glu | Leu | Ile | Ile | Gln | Ser | Ser | Asp | Leu | Met | Asn | Lys | Val | Arg | Val |      |
|     |     |     | 260 |     |     |     |     | 265 |     |     |     |     | 270 |     |     |      |
| ttg | ttt | aac | ttc | aat | aat | gat | ttg | ggc | tct | ggt | tcg | tgg | gct | gtg | caa | 864  |
| Leu | Phe | Asn | Phe | Asn | Asn | Asp | Leu | Gly | Ser | Gly | Ser | Trp | Ala | Val | Gln |      |
|     |     | 275 |     |     |     |     | 280 |     |     |     |     | 285 |     |     |     |      |
| ccc | gag | agc | gat | ccg | tcc | gct | ctt | tgg | ctc | act | gat | cca | tcg | tct | gca | 912  |
| Pro | Glu | Ser | Asp | Pro | Ser | Ala | Leu | Trp | Leu | Thr | Asp | Pro | Ser | Ser | Ala |      |
|     | 290 |     |     |     |     | 295 |     |     |     |     | 300 |     |     |     |     |      |
| gct | gta | caa | gtc | aaa | gat | tta | aat | aca | gtt | gag | gca | aat | tca | gtt | cca | 960  |
| Ala | Val | Gln | Val | Lys | Asp | Leu | Asn | Thr | Val | Glu | Ala | Asn | Ser | Val | Pro |      |
| 305 |     |     |     |     | 310 |     |     |     |     | 315 |     |     |     |     | 320 |      |
| tca | agt | aat | agt | agt | aag | caa | gtt | gta | ttt | gat | aat | gag | aat | aat | ggt | 1008 |
| Ser | Ser | Asn | Ser | Ser | Lys | Gln | Val | Val | Phe | Asp | Asn | Glu | Asn | Asn | Gly |      |
|     |     |     |     | 325 |     |     |     |     | 330 |     |     |     |     | 335 |     |      |
| cac | agt | tgt | gat | aat | cag | caa | cag | cac | cat | tct | cgg | caa | caa | aca | caa | 1056 |
| His | Ser | Cys | Asp | Asn | Gln | Gln | Gln | His | His | Ser | Arg | Gln | Gln | Thr | Gln |      |
|     |     |     | 340 |     |     |     |     | 345 |     |     |     |     | 350 |     |     |      |
| gga | ttt | ttt | aca | agg | gag | ttg | aac | ttt | tca | gaa | ttc | ggg | ttt | gat | gga | 1104 |
| Gly | Phe | Phe | Thr | Arg | Glu | Leu | Asn | Phe | Ser | Glu | Phe | Gly | Phe | Asp | Gly |      |
|     |     | 355 |     |     |     |     | 360 |     |     |     |     | 365 |     |     |     |      |
| agt | agt | aat | aat | agg | aat | ggg | aat | tca | tca | ctt | tct | tgc | aag | cca | gag | 1152 |
| Ser | Ser | Asn | Asn | Arg | Asn | Gly | Asn | Ser | Ser | Leu | Ser | Cys | Lys | Pro | Glu |      |
|     | 370 |     |     |     |     | 375 |     |     |     |     | 380 |     |     |     |     |      |
| tcg | ggg | gaa | atc | ttg | aat | ttt | ggt | gat | agc | act | aag | aaa | agt | gca | aat | 1200 |
| Ser | Gly | Glu | Ile | Leu | Asn | Phe | Gly | Asp | Ser | Thr | Lys | Lys | Ser | Ala | Asn |      |
| 385 |     |     |     |     | 390 |     |     |     |     | 395 |     |     |     |     | 400 |      |
| ggg | aac | tta | ttt | tcc | ggt | cag | tct | cat | ttt | ggt | gca | ggg | gag | gag | aat | 1248 |
| Gly | Asn | Leu | Phe | Ser | Gly | Gln | Ser | His | Phe | Gly | Ala | Gly | Glu | Glu | Asn |      |
|     |     |     |     | 405 |     |     |     |     | 410 |     |     |     |     | 415 |     |      |
| aag | aag | aag | aaa | agg | tca | cct | gct | tcc | aga | gga | agc | aat | gaa | gaa | gga | 1296 |
| Lys | Lys | Lys | Lys | Arg | Ser | Pro | Ala | Ser | Arg | Gly | Ser | Asn | Glu | Glu | Gly |      |
|     |     |     | 420 |     |     |     |     | 425 |     |     |     |     | 430 |     |     |      |
| atg | ctt | tca | ttt | gtt | tca | ggt | aca | atc | ttg | cct | gca | gct | tct | ggt | gcg | 1344 |
| Met | Leu | Ser | Phe | Val | Ser | Gly | Thr | Ile | Leu | Pro | Ala | Ala | Ser | Gly | Ala |      |
|     |     | 435 |     |     |     |     | 440 |     |     |     |     | 445 |     |     |     |      |
| atg | aag | tca | agt | gga | tgt | gtc | ggt | gaa | gac | tcc | tct | gat | cat | tcg | gat | 1392 |
| Met | Lys | Ser | Ser | Gly | Cys | Val | Gly | Glu | Asp | Ser | Ser | Asp | His | Ser | Asp |      |
|     | 450 |     |     |     |     | 455 |     |     |     |     | 460 |     |     |     |     |      |
| ctt | gag | gcc | tca | gtg | gtg | aaa | gaa | gct | gaa | agt | agt | aga | gtt | gta | gaa | 1440 |
| Leu | Glu | Ala | Ser | Val | Val | Lys | Glu | Ala | Glu | Ser | Ser | Arg | Val | Val | Glu |      |
| 465 |     |     |     |     | 470 |     |     |     |     | 475 |     |     |     |     | 480 |      |
| ccc | gaa | aag | agg | cca | aag | aag | cga | gga | agg | aag | cca | gca | aat | gga | cgt | 1488 |
| Pro | Glu | Lys | Arg | Pro | Lys | Lys | Arg | Gly | Arg | Lys | Pro | Ala | Asn | Gly | Arg |      |
|     |     |     |     | 485 |     |     |     |     | 490 |     |     |     |     | 495 |     |      |
| gag | gaa | cct | ttg | aat | cac | gtc | gaa | gca | gag | agg | caa | agg | aga | gag | aaa | 1536 |
| Glu | Glu | Pro | Leu | Asn | His | Val | Glu | Ala | Glu | Arg | Gln | Arg | Arg | Glu | Lys |      |
|     |     |     | 500 |     |     |     |     | 505 |     |     |     |     | 510 |     |     |      |
| tta | aac | caa | agg | ttc | tac | gct | tta | aga | gct | gtt | gtt | ccg | aat | gtg | tcc | 1584 |
| Leu | Asn | Gln | Arg | Phe | Tyr | Ala | Leu | Arg | Ala | Val | Val | Pro | Asn | Val | Ser |      |
|     |     | 515 |     |     |     |     | 520 |     |     |     |     | 525 |     |     |     |      |
| aag | atg | gac | aag | gca | tca | ctg | ctt | gga | gat | gca | att | tca | tat | att | aat | 1632 |
| Lys | Met | Asp | Lys | Ala | Ser | Leu | Leu | Gly | Asp | Ala | Ile | Ser | Tyr | Ile | Asn |      |
|     | 530 |     |     |     |     | 535 |     |     |     |     | 540 |     |     |     |     |      |
| gag | ctg | aag | ttg | aag | ctt | caa | act | aca | gaa | aca | gat | aga | gaa | gac | ttg | 1680 |
| Glu | Leu | Lys | Leu | Lys | Leu | Gln | Thr | Thr | Glu | Thr | Asp | Arg | Glu | Asp | Leu |      |
| 545 |     |     |     |     | 550 |     |     |     |     | 555 |     |     |     |     | 560 |      |
| aag | agc | caa | ata | gaa | gat | ttg | aag | aaa | gaa | tta | gat | agt | aaa | gac | tca | 1728 |

-continued

```
Lys Ser Gln Ile Glu Asp Leu Lys Lys Glu Leu Asp Ser Lys Asp Ser
                565                 570                 575 agg cgc cct ggt cct cca cca cca aat caa gat cac aag atg tct agc    1776
Arg Arg Pro Gly Pro Pro Pro Pro Asn Gln Asp His Lys Met Ser Ser
            580                 585                 590 cat act gga agc aag att gta gat gtg gat ata gat gtt aag ata att    1824
His Thr Gly Ser Lys Ile Val Asp Val Asp Ile Asp Val Lys Ile Ile
        595                 600                 605 gga tgg gat gcg atg att cgt ata caa tgt aat aaa aag aac cat cca    1872
Gly Trp Asp Ala Met Ile Arg Ile Gln Cys Asn Lys Lys Asn His Pro
    610                 615                 620 gct gca agg tta atg gta gcc ctc aag gag tta gat cta gat gtg cac    1920
Ala Ala Arg Leu Met Val Ala Leu Lys Glu Leu Asp Leu Asp Val His
625                 630                 635                 640 cat gcc agt gtt tca gtg gtg aat gat ttg atg atc caa caa gcc aca    1968
His Ala Ser Val Ser Val Val Asn Asp Leu Met Ile Gln Gln Ala Thr
                645                 650                 655 gtg aaa atg ggt agc aga ctt tac acg gaa gag caa ctt agg ata gca    2016
Val Lys Met Gly Ser Arg Leu Tyr Thr Glu Glu Gln Leu Arg Ile Ala
            660                 665                 670 ttg aca tcc aga gtt gct gaa aca cgc taa                            2046
Leu Thr Ser Arg Val Ala Glu Thr Arg
        675                 680

<210> SEQ ID NO 4
<211> LENGTH: 681
<212> TYPE: PRT
<213> ORGANISM: Nicotiana tabacum

<400> SEQUENCE: 4

Met Thr Asp Tyr Ser Leu Pro Thr Met Asn Leu Trp Asn Thr Ser Gly
1               5                   10                  15

Thr Thr Asp Asp Asn Val Thr Met Met Glu Ala Phe Met Ser Ser Asp
                20                  25                  30

Leu Thr Ser Phe Trp Ala Thr Ser Asn Ser Thr Ala Val Ala Ala Val
            35                  40                  45

Thr Ser Asn Ser Asn His Ile Pro Val Asn Thr Pro Thr Val Leu Leu
        50                  55                  60

Pro Ser Ser Cys Ala Ser Thr Val Thr Ala Val Ala Val Asp Ala Ser
65                  70                  75                  80

Lys Ser Met Ser Phe Phe Asn Gln Glu Thr Leu Gln Gln Arg Leu Gln
                85                  90                  95

Thr Leu Ile Asp Gly Ala Arg Glu Thr Trp Thr Tyr Ala Ile Phe Trp
            100                 105                 110

Gln Ser Ser Ala Val Asp Leu Thr Ser Pro Phe Val Leu Gly Trp Gly
        115                 120                 125

Asp Gly Tyr Tyr Lys Gly Glu Glu Asp Lys Ala Asn Arg Lys Leu Ala
    130                 135                 140

Val Ser Ser Pro Ala Tyr Ile Ala Glu Gln His Arg Lys Lys Val
145                 150                 155                 160

Leu Arg Glu Leu Asn Ser Leu Ile Ser Gly Thr Gln Thr Gly Thr Asp
                165                 170                 175

Asp Ala Val Asp Glu Val Thr Asp Thr Glu Trp Phe Phe Leu Ile
            180                 185                 190

Ser Met Thr Gln Ser Phe Val Asn Gly Ser Gly Leu Pro Gly Gln Ala
        195                 200                 205

Leu Tyr Asn Ser Ser Pro Ile Trp Val Ala Gly Ala Glu Lys Leu Ala
```

-continued

```
             210                 215                 220
Ala Ser His Cys Glu Arg Ala Arg Gln Ala Gln Gly Phe Gly Leu Gln
225                 230                 235                 240

Thr Met Val Cys Ile Pro Ser Ala Asn Gly Val Val Glu Leu Gly Ser
                245                 250                 255

Thr Glu Leu Ile Ile Gln Ser Ser Asp Leu Met Asn Lys Val Arg Val
                    260                 265                 270

Leu Phe Asn Phe Asn Asn Asp Leu Gly Ser Gly Ser Trp Ala Val Gln
                275                 280                 285

Pro Glu Ser Asp Pro Ser Ala Leu Trp Leu Thr Asp Pro Ser Ser Ala
        290                 295                 300

Ala Val Gln Val Lys Asp Leu Asn Thr Val Glu Ala Asn Ser Val Pro
305                 310                 315                 320

Ser Ser Asn Ser Ser Lys Gln Val Val Phe Asp Asn Glu Asn Asn Gly
                    325                 330                 335

His Ser Cys Asp Asn Gln Gln Gln His His Ser Arg Gln Gln Thr Gln
                340                 345                 350

Gly Phe Phe Thr Arg Glu Leu Asn Phe Ser Glu Phe Gly Phe Asp Gly
                355                 360                 365

Ser Ser Asn Asn Arg Asn Gly Asn Ser Ser Leu Ser Cys Lys Pro Glu
        370                 375                 380

Ser Gly Glu Ile Leu Asn Phe Gly Asp Ser Thr Lys Lys Ser Ala Asn
385                 390                 395                 400

Gly Asn Leu Phe Ser Gly Gln Ser His Phe Gly Ala Gly Glu Glu Asn
                    405                 410                 415

Lys Lys Lys Lys Arg Ser Pro Ala Ser Arg Gly Ser Asn Glu Glu Gly
                420                 425                 430

Met Leu Ser Phe Val Ser Gly Thr Ile Leu Pro Ala Ala Ser Gly Ala
                435                 440                 445

Met Lys Ser Ser Gly Cys Val Gly Glu Asp Ser Ser Asp His Ser Asp
        450                 455                 460

Leu Glu Ala Ser Val Val Lys Glu Ala Glu Ser Ser Arg Val Val Glu
465                 470                 475                 480

Pro Glu Lys Arg Pro Lys Lys Arg Gly Arg Lys Pro Ala Asn Gly Arg
                    485                 490                 495

Glu Glu Pro Leu Asn His Val Glu Ala Glu Arg Gln Arg Arg Glu Lys
                500                 505                 510

Leu Asn Gln Arg Phe Tyr Ala Leu Arg Ala Val Val Pro Asn Val Ser
                515                 520                 525

Lys Met Asp Lys Ala Ser Leu Leu Gly Asp Ala Ile Ser Tyr Ile Asn
        530                 535                 540

Glu Leu Lys Leu Lys Leu Gln Thr Thr Glu Thr Asp Arg Glu Asp Leu
545                 550                 555                 560

Lys Ser Gln Ile Glu Asp Leu Lys Lys Glu Leu Asp Ser Lys Asp Ser
                    565                 570                 575

Arg Arg Pro Gly Pro Pro Pro Asn Gln Asp His Lys Met Ser Ser
                580                 585                 590

His Thr Gly Ser Lys Ile Val Asp Val Asp Ile Asp Val Lys Ile Ile
                595                 600                 605

Gly Trp Asp Ala Met Ile Arg Ile Gln Cys Asn Lys Lys Asn His Pro
        610                 615                 620

Ala Ala Arg Leu Met Val Ala Leu Lys Glu Leu Asp Leu Asp Val His
625                 630                 635                 640
```

His Ala Ser Val Ser Val Asn Asp Leu Met Ile Gln Gln Ala Thr
            645                 650                 655

Val Lys Met Gly Ser Arg Leu Tyr Thr Glu Glu Gln Leu Arg Ile Ala
        660                 665                 670

Leu Thr Ser Arg Val Ala Glu Thr Arg
        675                 680

<210> SEQ ID NO 5
<211> LENGTH: 702
<212> TYPE: DNA
<213> ORGANISM: Artificial Sequence
<220> FEATURE:
<223> OTHER INFORMATION: cDNA sequence of NtERF2

<400> SEQUENCE: 5

```
atgtatcaac caatttcgac cgagctacct ccgacgagtt tcagtagtct catgccatgt      60
ttgacggata catggggtga cttgccgtta aaagttgatg attccgaaga tatggtaatt     120
tatgggctct taagtgacgc tttaactgcc ggatggacgc cgtttaattt aacgtccacc     180
gaaataaaag ccgagccgag ggaggagatt gagccagcta cgattcctgt tccttcagtg     240
gctccacctg cggagactac gacggctcaa gccgttgttc ccaaggggag gcattatagg     300
ggcgttaggc aaaggccgtg ggggaaattt gcggcggaaa taagggaccc agctaaaaac     360
ggcgcacggg tttggctagg gacttatgag acggctgaag aagccgcgct cgcttatgat     420
aaagcagctt acaggatgcg cggctccaag gctctattga attttccgca taggatcggc     480
ttaaatgagc ctgaaccggt tagactaacc gctaagagac gatcacctga accggctagc     540
tcgtcaatat catcggcttt ggaaaatggc tcgccgaaac ggaggagaaa agctgtagcg     600
gctaagaagg ctgaattaga agtgcaaagc cgatcaaatg ctatgcaagt tgggtgccag     660
atggaacaat ttccagttgg cgagcagcta ttagtcagtt aa                       702
```

<210> SEQ ID NO 6
<211> LENGTH: 705
<212> TYPE: DNA
<213> ORGANISM: Artificial Sequence
<220> FEATURE:
<223> OTHER INFORMATION: NtERF5 cDNA

<400> SEQUENCE: 6

```
atgtcaagta actcaagccc actagaaata gacacttcat tttcacattc caacttcttc      60
tttctccaag atcaatcacc aatttttacaa tgggatgatg atcttttctt caatgatcca     120
tggtttgatg atgatcaatc accaattata ccatgtaact cagagaaaga tgaaaatcat     180
caagtatttg aagaatcctc agacaataca atcatgtcaa aaggaagtag ccatggtcaa     240
gaattagaag aggtaacatc ccaagaagaa aagaaaaaag aagaagaaga aaaacactat     300
ataggagtta gaaaaaggcc atggggtaaa tatgcagcag aaataagaga ttcaacaaga     360
aatggaatta gggtttggtt agggacattt gatacagctg aagaagctgc tttagcttat     420
gatcaagctg cattatcgat gagaggtcct tggtctcttc ttaattttcc attggagaaa     480
gtcaagaaat cacttgaaaa aattgagtat tcttgtaaag atggattgtc tcctgctgct     540
gttctaaaag ctactcataa aacaaggaga gtgaagcata aagaagtag tagaaagaaa     600
aagaataaag aaactcataa tgttattgtt tttgaggact ggggtgctga gttattagaa     660
gagcttttaa tgacttcatc acaacattcg tgtcgaaggg actga                    705
```

```
<210> SEQ ID NO 7
<211> LENGTH: 57
<212> TYPE: DNA
<213> ORGANISM: Artificial Sequence
<220> FEATURE:
<223> OTHER INFORMATION: NtPMT1a promoter

<400> SEQUENCE: 7
ctgcacgttg taatgaattt ttaactatta tattatatcg agttgcgccc tccactc        57

<210> SEQ ID NO 8
<211> LENGTH: 57
<212> TYPE: DNA
<213> ORGANISM: Artificial Sequence
<220> FEATURE:
<223> OTHER INFORMATION: Synthesized

<400> SEQUENCE: 8 cttcttttt atatctaaaa taaagataat aaaatattcg attttctccc tccactc         57

<210> SEQ ID NO 9
<211> LENGTH: 14
<212> TYPE: DNA
<213> ORGANISM: Artificial Sequence
<220> FEATURE:
<223> OTHER INFORMATION: G-Box

<400> SEQUENCE: 9
ctgcacgttg taat        14

<210> SEQ ID NO 10
<211> LENGTH: 14
<212> TYPE: DNA
<213> ORGANISM: Artificial Sequence
<220> FEATURE:
<223> OTHER INFORMATION: Mutant G-Box

<400> SEQUENCE: 10
ctgcttaatg taat        14
```